United States Patent [19]

Jacobson

[11] Patent Number: 5,109,014
[45] Date of Patent: Apr. 28, 1992

[54] N-ARYL-3-ARYL-4-SUBSTITUTED-2,3,4,5-TETRAHYDRO-1H-PYRAZOLE-1-CARBOXAMIDES

[76] Inventor: Richard M. Jacobson, 11 Deerpath Rd., Chalfont, Pa. 18914

[21] Appl. No.: 624,808

[22] Filed: Dec. 10, 1990

[51] Int. Cl.$^5$ .................... C07D 231/04; A01N 43/56
[52] U.S. Cl. .................................... 514/403; 514/404; 548/356; 548/358
[58] Field of Search ............... 548/356, 358; 514/403, 514/404

[56] References Cited

U.S. PATENT DOCUMENTS

| 3,948,936 | 4/1976 | Cross et al. ............... 548/356 |
| 4,156,007 | 5/1979 | van Daalen et al. ............. 514/403 |
| 4,624,961 | 11/1986 | Welstead, Jr. ................ 514/503 |
| 4,863,947 | 9/1989 | Jacobson ..................... 514/403 |

OTHER PUBLICATIONS

Chemical Abstracts vol. 93 No. 25, Abst. No. 239347a.
Chemical Abstracts vol. 100 No. 23, Abst. No. 19178a.

Primary Examiner—Jose G. Dees
Assistant Examiner—M. S. H. Gabilan

[57] ABSTRACT

This invention relates to novel N-aryl-3-aryl-4-substituted-2,3,4,5-tetrahydro-1H-pyrazole-1-carboxamide compounds which are useful as pesticides, compositions containing those compounds, methods of controlling pests and processes for preparing these compounds.

34 Claims, No Drawings

N-ARYL-3-ARYL-4-SUBSTITUTED-2,3,4,5-TETRAHYDRO-1H-PYRAZOLE-1-CARBOXAMIDES

This invention relates to novel N-aryl-3-ary-4-substituted-2,3,4,5-tetrahydro-1H-pyrazole-1-carboxamides which are useful as pesticides, compositions containing those compounds, methods of controlling pests and processes for preparing the compounds of the present invention.

The search for pesticides which have a combination of excellent pesticidal activity and essentially no other toxicity is a continuing one due to recognition of the possible toxicity to animals and humans of many known pesticides.

Presently known dihydropyrazole insecticides, such as those disclosed in U.S. Pat. Nos. 4,863,947, 4,070,365, 4,174,393, 4,439,440, 4,407,813, and 4,156,007, are believed to be subject to problems with photostability and/or biodegradability. These compounds tend to degrade faster than is desirable when applied to the external parts of plants due to the action of sunlight on these compounds. Moreover, when known compounds are applied to the soil, they exhibit poor biodegradability causing an undesirable residue to remain in the soil.

This invention relates to N-aryl-3-aryl-4-substituted-2,3,4,5-tetrahydro-1H-pyrazole-1-carboxamides. It is believed this reduction of the 4,5-dihydro-1H-pyrazole ring may sufficiently alter metabolic pathway transformations in plants and insects to provide the necessary differentiation which allows for high insect toxicity and low mammalian toxicity. It is further believed to permit appropriate biodegradation.

It is therefore an object of the invention to provide novel compounds, and compositions containing the compounds, which possess pesticidal activity. It is another object of the present invention to provide compounds which demonstrate improved differentiation between insecticidal activity and mammalian toxicity. It is a further object of the invention to provide methods for the synthesis of 1-substituted-4-substituted-2,3,4,5-tetrahydro-1H-pyrazoles. It is still another object of the present invention to provide methods for controlling pests and insects using the novel compounds.

These and other objects of the invention will become apparent to those skilled in the art from the following description.

In accordance with the present invention, there are provided compounds having the formula:

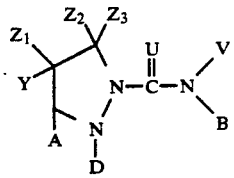

wherein
A is aryl or aromatic heterocyclyl;
B is aryl or aromatic heterocyclyl;
U is oxygen (O) or sulfur (S);
V is hydrogen, alkyl, alkoxyalkyl, alkylthioalkyl, formyl, alkylcarbonyl, alkylaminocarbonyl, carboxy, alkoxycarbonyl, alkenyloxycarbonyl, alkynyloxycarbonyl, phenyloxycarbonyl, alkoxycarbonylcarbonyl, alkoxy, phenyloxy, alkoxycarbonylalkoxy, alkoxycarbonyloxy, alkylthio, alkylsulfonyl, phenylthio, alkoxycarbonylalkylthio or alkoxycarbonylthio;
D is hydrogen, alkoxycarbonyl, alkylsulfonyl, alkylcarbonyl or alkyl; or
D and V together may form E wherein
E is alkylidene, carbonyl, dicarbonyl or carbonylalkylidene;
Y is phenyl, alkyl, haloalkyl, hydroxyalkyl, alkoxyalkyl, alkoxyalkoxyalkyl, alkylcarbonyloxyalkyl, (alkylthio)alkyl, alkylsulfinylalkyl, cyanoalkyl, carboxyalkyl, alkoxycarbonylalkyl, alkenyl, haloalkenyl, formyl, alkylcarbonyl, haloalkylcarbonyl, phenylcarbonyl, alkoxycarbonylcarbonyl, halocarbonyl, aminocarbonyl, N-alkylaminocarbonyl, N,N-dialkylaminocarbonyl, pyrrolidin-1-ylcarbonyl, piperidin-1-ylcarbonyl, morpholin-1-ylcarbonyl, pyrazol-1-ylcarbonyl, imidazol-1-ylcarbonyl, pyrrol-1-ylcarbonyl, hydroxyalkylaminocarbonyl, thioalkylaminocarbonyl, phenylaminocarbonyl, carboxy, alkoxycarbonyl, alkoxyalkoxycarbonyl, alkoxyalkoxyalkoxycarbonyl, haloalkoxycarbonyl, cyanoalkoxycarbonyl, alkylthioalkoxycarbonyl, (alkylthio)thiocarbonyl, pyridyl, oxazol-2-yl, 2-benzoxazolyl, isothiocyanato (—NCS), isocyano (—NC), unsubstituted or substituted amino (—NR$^1$R$^2$), alkanoyloxy, alkoxy, phenyloxy, alkylthio, alkylsulfonyl or phenylthio;

wherein R$^1$ and R$^2$ are independently hydrogen, cyano, alkyl, phenylalkyl, formyl, alkylcarbonyl, alkenylcarbonyl, alkynylcarbonyl, alkoxyalkylcarbonyl, phenylcarbonyl, phenylalkylcarbonyl, phenylalkenylcarbonyl, phenylalkynylcarbonyl, alkoxycarbonyl, alkoxyalkoxycarbonyl, alkenyloxycarbonyl, alkynyloxycarbonyl, alkanoylalkoxycarbonyl, alkoxycarbonylalkoxycarbonyl, carboxyalkoxycarbonyl, phenyloxycarbonyl, phenylalkoxycarbonyl, alkylthiocarbonyl, alkenylthiocarbonyl, alkynylthiocarbonyl, alkanoylalkylthiocarbonyl, alkoxycarbonylalkylthiocarbonyl, alkylthiocarbonylalkoxycarbonyl, alkylthiocarbonylalkylthiocarbonyl, carbonylalkylthiocarbonyl, phenylthiocarbonyl, phenylalkylthiocarbonyl, N-alkylaminocarbonyl, N,N-dialkylaminocarbonyl, N-phenyl-N-alkylaminocarbonyl, N-(phenylcarbonyl)aminocarbonyl, dialkylphosphoryl (—P(O)(OR)$_2$), dialkylthiophosphoryl (—P(S)(OR)$_2$), alkylsulfonyl, alkenylsulfonyl, alkynylsulfonyl, N-alkylaminosulfonyl, N,N-dialkylaminosulfonyl, phenylsulfonyl, or heterocyclyl; or
R$^1$ and R$^2$ together with the nitrogen to which they are attached may form a 5- or 6-membered ring;
$Z_1$ is hydrogen or alkyl;
$Z_2$ is hydrogen or alkyl;
$Z_3$ is hydrogen or alkyl; and
agronomically acceptable salts thereof.

Alkyl means straight and branched alkyl groups, for example (C$_1$-C$_6$)alkyl such as methyl, ethyl, n-propyl, isopropyl, n-butyl, isobutyl, s-butyl, t-butyl or n-pentyl. An alkyl portion of any one of the substituents listed above for V, Y and Z or of the substituents on the aryl rings listed below is optionally substituted by one to eight halogens to form groups such as trifluoromethyl, bromodifluoromethyl, 1,1,2,2,2-pentafluoroethyl, 1,1,2,2-tetrafluoroethyl, chloromethyl, dichloromethyl, trichloromethyl, difluoromethyl, 2-bromoethyl, 2-chloroethyl, 3-bromopropyl, 2-chloro-1,1,2-trifluoroethyl, 2-bromo-1,1,2,2-tetrafluoroethyl, or 1,1,2,3,3,3-hexafluoropropyl; or optionally substituted by cyano to form groups such as 3-cyanopropyl.

Hydroxyalkyl is, for example, hydroxy($C_1$–$C_6$)alkyl such as hydroxymethyl, 1-hydroxyethyl or 2-hydroxyethyl.

Alkenyl is, for example, ($C_2$–$C_6$)alkenyl such as vinyl and allyl.

Haloalkenyl is for example ($C_2$–$C_6$)alkenyl such as 2,2-dibromovinyl, 2,2-dichlorovinyl, 2,2-difluorovinyl or 2-bromovinyl.

Alkynyl is, for example, ($C_3$–$C_6$)alkynyl such as propargyl.

Alkoxyalkyl is, for example ($C_1$–$C_6$)alkoxy($C_1$–$C_6$)alkyl such as methoxymethyl, methoxyethyl, 4-methoxybutyl.

Alkoxyalkoxyalkyl is, for example, ($C_1$–$C_6$)alkoxy($C_1$–$C_6$)alkoxy($C_1$–$C_6$)alkoxy such as 2-methoxyethoxymethyl.

Alkylcarbonyloxyalkyl is, for example, ($C_1$–$C_6$)alkylcarbonyloxy($C_1$–$C_6$)alkyl such as 2-(methylcarbonyloxy)ethyl or methylcarbonyloxymethyl.

Alkylthioalkyl is, for example, ($C_1$–$C_6$)alkylthio($C_1$–$C_6$)alkyl such as 2-methylthio)ethyl or 2-(ethylthio)ethyl.

Alkylsulfinylalkyl is, for example, ($C_1$–$C_6$)alkylsulfinyl($C_1$–$C_6$)alkyl such as 2-(methylsulfinyl)ethyl.

Phenylalkyl is, for example, phenyl($C_1$–$C_6$)alkyl such as benzyl and 2-phenylethyl.

Carboxyalkyl is, for example, carboxy($C_1$–$C_6$)alkyl such as carboxymethyl.

Alkoxycarbonylalkyl is, for example, ($C_1$–$C_6$)alkoxycarbonyl($C_1$–$C_6$)alkyl such as methoxycarbonylmethyl.

Alkylcarbonyl is, for example, ($C_1$–$C_6$)alkylcarbonyl such as methylcarbonyl (acetyl), ethylcarbonyl, n-propylcarbonyl, isopropylcarbonyl, n-butylcarbonyl, isobutylcarbonyl, t-butylcarbonyl, n-pentylcarbonyl, chloromethylcarbonyl, trichloromethylcarbonyl, trifluoromethylcarbonyl, 3-chloropropylcarbonyl, 4-chlorobutylcarbonyl, pentafluoroethylcarbonyl and heptafluoropropylcarbonyl.

Alkenylcarbonyl is, for example, ($C_2$–$C_6$)alkenylcarbonyl such as vinylcarbonyl, 1-methylvinylcarbonyl, 2-methylvinylcarbonyl, 2,2-dimethylvinylcarbonyl and 1,2,2-trichlorovinylcarbonyl.

Alkynylcarbonyl is, for example, ($C_2$–$C_6$)alkynylcarbonyl.

Alkoxyalkylcarbonyl is, for example, ($C_1$–$C_6$)alkoxy($C_1$–$C_6$)alkylcarbonyl such as methoxymethylcarbonyl.

Phenylcarbonyl is, for example, unsubstituted phenylcarbonyl, 4-chlorophenylcarbonyl, 4-methylphenylcarbonyl or 4-trifluoromethylphenylcarbonyl Phenylalkylcarbonyl is, for example, phenyl($C_1$–$C_6$)alkylcarbonyl.

Phenylalkenylcarbonyl is, for example, phenyl($C_2$–$C_6$)alkenylcarbonyl such as phenylvinylcarbonyl (cinnamoyl).

Phenylalkynylcarbonyl is, for example, phenyl($C_2$–$C_6$)alkynyl.

Alkylaminocarbonyl is, for example, mono($C_1$–$C_6$)alklyaminocarbonyl, such as methylaminocarbonyl, or di($C_1$–$C_6$)alkylaminocarbonyl such as dimethylaminocarbonyl.

Alkoxycarbonyl is for example, ($C_1$–$C_6$)alkoxycarbonyl such as methoxycarbonyl (carbomethoxy), ethoxycarbonyl (carboethoxy), n-propyloxycarbonyl, isopropyloxycarbonyl, n-butyloxycarbonyl, isobutyloxycarbonyl, t-butyloxycarbonyl, n-pentyloxycarbonyl, cyanomethoxycarbonyl, 2-cyanoethoxycarbonyl, 2-bromoethoxycarbonyl, 2-chloroethoxycarbonyl, 2,2,2-trifluoroethoxycarbonyl, 2,2,2-trichloroethoxycarbonyl, 3-bromopropyloxycarbonyl, 3-chloropropyloxycarbonyl and 4-chlorobutyloxycarbonyl.

Alkenyloxycarbonyl is, for example, ($C_2$–$C_6$)alkenyloxycarbonyl such as vinyloxycarbonyl and allyloxycarbonyl.

Alkynyloxycarbonyl is, for example, ($C_3$–$C_6$)alkynyloxycarbonyl such as propargyloxycarbonyl.

Alkoxyalkoxycarbonyl is, for example, ($C_1$–$C_6$)alkoxy($C_1$–$C_6$)alkoxycarbonyl such as methoxyethoxycarbonyl.

Alkoxyalkoxyalkoxycarbonyl is, for example, ($C_1$–$C_6$)alkoxy($C_1$–$C_6$)alkoxy($C_1$–$C_6$)alkoxycarbonyl such as 2-(2-(methoxy)ethoxy)ethoxycarbonyl.

Alkanoylalkoxycarbonyl is, for example, ($C_1$–$C_6$)alkanoyl($C_1$–$C_6$)alkoxycarbonyl such as methylcarbonylmethoxycarbonyl.

Alkoxycarbonylalkoxycarbonyl is, for example, ($C_1$–$C_6$)alkoxycarbonyl, ($C_1$–$C_6$)alkoxycarbonyl such as ethoxycarbonylmethoxycarbonyl and ethoxycarbonylethoxycarbonyl.

Carboxyalkoxycarbonyl is, for example, carboxy($C_1$–$C_6$)alkoxycarbonyl such as carboxyethoxycarbonyl and carboxypropoxycarbonyl.

Alkoxycarbonylcarbonyl is for example, ($C_1$–$C_6$)alkoxycarbonylcarbonyl such as methoxycarbonylcarbonyl.

Halocarbonyl is, for example, chlorocarbonyl.

Phenylalkoxycarbonyl is, for example, phenyl($C_1$–$C_6$)alkoxycarbonyl such as benzyloxycarbonyl and 2-phenylethoxycarbonyl.

(Alkylthio)carbonyl is, for example, (($C_1$–$C_6$)alkylthio)carbonyl such as (methylthio)carbonyl, (ethylthio)carbonyl, (n-propylthio)carbonyl, and (n-butylthio)carbonyl.

(Alkenylthio)carbonyl is, for example, (($C_3$–$C_6$)alkylthio)carbonyl.

(Alkynylthio)carbonyl is, for example, (($C_3$–$C_6$)alkynylthio)carbonyl.

Alkylthioalkoxycarbonyl is, for example, ($C_1$–$C_6$)alkylthio($C_1$–$C_6$)alkoxycarbonyl such as methylthiomethoxycarbanyl.

(Alkylthio)thiocarbonyl is, for example, (($C_1$–$C_6$)alkylthio)thiocarbonyl such as (methylthio)thiocarbonyl.

Alkylcarbonyl(alkylthio)carbonyl is, for example, ($C_1$–$C_6$)alkyl carbonyl($C_1$–$C_6$)alkylthio)carbonyl.

Alkoxycarbonyl(alkylthio)carbonyl is, for example, ($C_1$–$C_6$)alkoxycarbonyl($C_1$–$C_6$)alkylthio)carbonyl.

(Alkylthio)carbonylalkoxycarbonyl is, for example, (($C_1$–$C_6$)alkylthio)carbonyl($C_1$–$C_6$)alkoxycarbonyl.

(Alkylthio)carbonyl(alkylthio)carbonyl is, for example, (($C_1$–$C_6$)alkylthio)carbonyl(($C_1$–$C_6$)alkylthio)carbonyl.

Carboxy(alkylthio)carbonyl is, for example, carboxy(($C_1$–$C_6$)-alkylthio)carbonyl.

(Phenylalkylthio)carbonyl is, for example, (phenyl($C_1$–$C_6$)alkylthio)carbonyl.

N-alkylaminocarbonyl is, for example, N-($C_1$–$C_6$)alkylaminocarbonyl such as methylaminocarbonyl.

N,N-dialkylaminocarbonyl is, for example, N,N-di($C_1$–$C_6$)alkylaminocarbonyl such as dimethylaminocarbonyl.

N-phenyl-N-alkylaminocarbonyl is, for example, N-phenyl-N-($C_1$–$C_6$)alkylaminocarbonyl such as N-methyl-N-(phenyl)aminocarbonyl.

N-(phenylcarbonyl)aminocarbonyl is, for example, N-(2,6-difluorophenylcarbonyl)aminocarbonyl.

Dialkylphosphoryl is, for example, di($C_1$-$C_6$)alkylphosphoryl such as diethylphosphoryl.

Dialkylthiophosphoryl is, for example, di($C_1$-$C_6$)alkylthiophosphoryl such as diethylthiophosphoryl.

Alkylsulfonyl is, for example, ($C_1$-$C_6$)alkylsulfonyl such as methylsulfonyl, n-butylsulfonyl, chloromethylsulfonyl, trifluoromethylsulfonyl and 2,2,2-trifluoroethylsulfonyl.

Alkenylsulfonyl is, for example, ($C_2$-$C_6$)alkenylsulfonyl such as vinylsulfonyl.

Alkynylsulfonyl is, for example, ($C_3$-$C_6$)alkynylsulfonyl.

N,N-dialkylaminosulfonyl is, for example, N,N-di($C_1$-$C_6$)alkylaminosulfonyl such as dimethylaminosulfonyl.

Alkoxy is, for example, ($C_1$-$C_6$)alkoxy such as methoxy, ethoxy, n-propyloxy, n-butyloxy, isobutyloxy, n-pentyloxy, trifluoromethoxy, difluoromethoxy, 1,1,2,2-tetrafluoroethoxy and 1,1,2,3,3,3-hexafluoropropyloxy.

Alkylthio is, for example, ($C_1$-$C_6$)alkylthio such as methylthio, n-propylthio, n-butylthio and 3-cyanopropylthio.

Alkoxycarbonylthio is, for example ($C_1$-$C_6$)alkoxycarbonylthio such as methoxycarbonylthio.

Phenylthio includes, for example, phenylthio and 2-nitrophenylthio.

Alkoxycarbonylalkylthio is, for example, ($C_1$-$C_6$)alkoxycarbonyl($C_1$-$C_6$)alkylthio such as 1-(methoxycarbonyl)prop-2-ylthio.

Heterocyclyl means five or six membered heterocyclic ring containing one, two or three heteroatoms such as oxygen, nitrogen or sulfur and includes saturated and aromatic rings, for example tetrahydrofuryl, furyl, pyridyl, pyrazinyl, oxazolyl, piperidyl, triazolyl, thienyl, thiazolyl or piperazyl. The heterocyyl ring is optionally substituted by one or two independently choses substituents, for example, nitro, ($C_1$-$C_6$)alkyl such as methyl and trifluoromethyl and halo such as chloro.

Aryl is an aromatic carbocyclic structure, for example, phenyl or naphthyl.

Naphthyl is optionally substituted by one or two independently chosen substituents, for example, nitro, ($C_1$-$C_6$)alkyl such as methyl and trifluoromethyl and halo such as chloro.

Phenyl is optionally substituted by one to three independently chosen substituents, for example, ($C_1$-$C_6$)alkyl, halo, hydroxy, ($C_1$-$C_6$)alkoxy, ($C_3$-$C_6$)alkenyloxy, ($C_3$-$C_6$)alkynyloxy, ($C_1$-$C_6$)alkoxy($C_1$-$C_6$)alkoxy, phenyl($C_1$-$C_6$)alkoxy, phenyloxy, pyridyloxy, mono($C_1$-$C_6$)alkylaminocarbonyloxy, di($C_1$-$C_6$)alkylaminocarbonyloxy, ($C_1$-$C_6$)alkanoyloxy, ($C_1$-$C_6$)alkoxycarbonyloxy, ($C_1$-$C_6$)alkylsulfonyloxy, ($C_1$-$C_6$)alkylthio, ($C_1$-$C_6$)alkoxy($C_1$-$C_6$)alkyl, ($C_1$-$C_6$)alkanoyl, ($C_1$-$C_6$)alkoxycarbonyl, nitro, ($C_1$-$C_6$)alkylsulfonyl, phenyl, cyano, isocyano (—NC), amino, mono($C_1$-$C_6$)alkylamino, di($C_1$-$C_6$)alkylamino, formylamino (—NHCHO), ($C_1$-$C_6$)alkanoylamino, phenylcarbonylamino, mono($C_1$-$C_6$)-alkylaminocarbonylamino, and di($C_1$-$C_6$)alkylaminocarbonylamino, such as 4-methyl, 4-ethyl, 4-propyl, 4-t-butyl, 4-trifluoromethyl, 4-dichloromethyl, 4-trichloromethyl, 4-fluoro, 4-bromo, 4-chloro, 4-iodo, 4-hydroxy, 4-methoxy, 4-ethoxy, 4-n-propyloxy, 4-isopropyloxy, 4-sec-butyloxy, 4-n-butyloxy, 4-isobutyloxy, 4-n-pentyloxy, 4-difluoromethoxy, 4-trifluoromethoxy, 4-(1,1,2,2-tetrafluoroethoxy), 4-bromodifluoromethoxy, 4-(1,1,2,3,3,3-hexafluoropropyloxy), 4-allyloxy, 4-propargyloxy, 4-methoxymethoxy, 4-benzyloxy, 4-(2-phenylethoxy), 4-phenyloxy, 4-(2-chloro-4-trifluoromethylphenyloxy), 4-(5-chloro-2-pyridyloxy), 4-(5-(trifluoromethyl)-2-pyridyloxy), 4-(3-chloro-5-(trifluoromethyl)-2-pyridyloxy), 4-methylaminocarbonyloxy, 4-N,N-dimethylaminocarbonyloxy), 4-acetoxy, 4-methoxycarbonyloxy, 4-methylsulfonyloxy, 4-trifluoromethylsulfonyloxy, 4-methylthio, 4-(1,1,2,2-tetrafluoroethylthio), 4-(2-ethoxyethyl), 4-acetyl, (i.e., methylcarbonyl), 4-ethylcarbonyl, 4-isopropylcarbonyl, 4-methoxycarbonyl, 4-ethoxycarbonyl, 4-isopropyloxycarbonyl, 4-nitro, 4-methylsulfonyl, 4-(1,1,2,2-tetrafluoroethylsulfonyl), 4-phenyl, 4-cyano, 4-isocyano, 4-amino, 4-methylamino, 4-dimethylamino, 4-formylamino, 4-acetamido, 4-trifluoroacetamido, 4-phenylcarbonylamino, 4-(4-chlorophenylcarbonylamino), 4-methylaminocarbonylamino, and 4-(di-n-propylaminocarbonylamino).

Halo means fluoro, chloro, bromo and iodo.

Agronomically acceptable salts include those known in the art, for example, metal salts such as sodium, potassium, calcium and magnesium; ammonium salts such as isopropylammonium; and trialkylsulfonium salts such as trimethylsulfonium.

Further, in accordance with the present invention, there are provided compositions containing compounds of the present invention and processes for preparing 1-substituted-4-substituted-2,3,4,5-tetrahydro-1H-pyrazoles of the present invention.

Preferably the compounds of the invention are compounds of Formula I

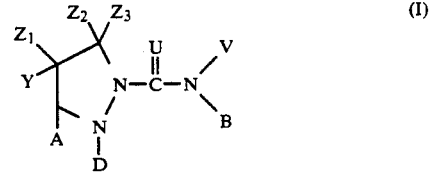

(I)

wherein

A and B are pyridyl, furyl, thiazolyl or naphthyl, each of which is optionally substituted by one or two independently chosen substituents selected from nitro, ($C_1$-$C_6$)alkyl, halo($C_1$-$C_6$)alkyl and halo;

phenyl or phenyl substituted by one to three substituents independently selected from ($C_1$-$C_6$)alkyl, halo($C_1$-$C_6$)alkyl, halo, ($C_1$-$C_6$)alkoxy, halo($C_1$-$C_6$)alkoxy, ($C_3$-$C_6$)alkenyloxy, ($C_3$-$C_6$)alkynyloxy, ($C_1$-$C_6$)alkoxy($C_1$-$C_6$)alkoxy, phenyl($C_1$-$C_6$)alkoxy, phenyloxy, pyridyloxy, mono($C_1$-$C_6$)alkylaminocarbonyloxy, di($C_1$-$C_6$)alkylaminocarbonyloxy, ($C_1$-$C_6$)alkanoyloxy, ($C_1$-$C_6$)alkoxycarbonyloxy, ($C_1$-$C_6$)alkylsulfonyloxy, ($C_1$-$C_6$)alkylthio, halo($C_1$-$C_6$)alkylthio, ($C_1$-$C_6$)alkoxy($C_1$-$C_6$)alkyl, ($C_1$-$C_6$)alkanoyl, ($C_1$-$C_6$)alkoxycarbonyl, nitro, ($C_1$-$C_6$)alkylsulfonyl, halo($C_1$-$C_6$)alkylsulfonyl, phenyl, hydroxy, cyano, isocyano, amino, mono($C_1$-$C_6$)alkylamino, di($C_1$-$C_6$)alkylamino, formylamino, ($C_1$-$C_6$)alkanoylamino, halo($C_1$-$C_6$)alkanoylamino, ($C_1$-$C_6$)alkoxycarbonylamino, phenylcarbonylamino, mono($C_1$-$C_6$)alkylaminocarbonylamino, and di($C_1$-$C_6$)alkylaminocarbonylamino;

U is oxygen or sulfur;

V is hydrogen, ($C_1$-$C_6$)alkyl, ($C_1$-$C_6$)alkoxy($C_1$-$C_6$)alkyl, formyl, ($C_1$-$C_6$)alkylcarbonyl, ($C_1$-$C_6$)alkylaminocarbonyl, ($C_1$-$C_6$)alkoxycarbonyl, ($C_3$-$C_6$)alkenyloxycarbonyl, phenyloxycarbonyl, ($C_1$-$C_6$)alkoxycarbonylcarbonyl, cyano($C_1$-$C_6$)alkylthio, ($C_1$-$C_6$)alkylthio, phenylthio, (C₁-C₆)alkoxycarbonyl(C₁-C₆)alkylthio or (C₁-C₆)alkoxycarbonylthio;

D is hydrogen, phenylcarbonyl, halophenylcarbonyl, phenylsulfonyl, halophenylsulfonyl, (C₁-C₆)alkylsulfonyl, (C₁-C₆)alkanoyl, halo(C₁-C₆)alkanoyl, (C₁-C₆)alkoxycarbonyl or (C₁-C₆)alkyl; or D and V together form E wherein E is alkylidene, carbonyl, dicarbonyl or carbonyl(C₁-C₆)alkylidene;

Y is phenyl, halophenyl, (C₁-C₆)alkyl, halo(C₁-C₆)alkyl, hydroxy(C₁-C₆)alkyl, (C₁-C₆)alkoxy(C₁-C₆)alkyl, (C₁-C₆)alkoxy(C₁-C₆)alkoxy(C₁-C₆)alkyl, (C₁-C₆)alkylcarbonyloxy(C₁-C₆)alkyl, ((C₁-C₆)alkylthio)(C₁-C₆)alkyl, (C₁-C₆)alkylsulfinyl(C₁-C₆)alkyl, cyano(C₁-C₆)alkyl, carboxy(C₁-C₆)alkyl, (C₁-C₆)alkoxycarbonyl(C₁-C₆)alkyl, (C₂-C₆)alkenyl, halo(C₂-C₆)alkenyl, formyl, (C₁-C₆)alkylcarbonyl, halo(C₁-C₆)alkylcarbonyl, phenylcarbonyl, (C₁-C₆)alkoxycarbonylcarbonyl, halocarbonyl, aminocarbonyl, N-(C₁-C₆)alkylaminocarbonyl, N,N-di(C₁-C₆)alkylaminocarbonyl, pyrrolidin-1-ylcarbonyl, piperidin-1-ylcarbonyl, morpholin-1-ylcarbonyl, pyrazol-1-ylcarbonyl, imidazol-1-ylcarbonyl, pyrrol-1-ylcarbonyl, hydroxy(C₁-C₆)alkylaminocarbonyl, thio(C₁-C₆)alkylaminocarbonyl, phenylaminocarbonyl, carboxy, (C₁-C₆)alkoxycarbonyl, (C₁-C₆)alkoxy(C₁-C₆)alkoxycarbonyl, (C₁-C₆)alkoxy(C₁-C₆)alkoxy(C₁-C₆)alkoxycarbonyl, halo(C₁-C₆)alkoxycarbonyl, cyano(C₁-C₆)alkoxycarbonyl, (C₁-C₆)alkylthio(C₁-C₆)alkoxycarbonyl, ((C₁-C₆)alkylthio)thiocarbonyl, pyridyl, oxazol-2-yl, 2-benzoxazolyl, isothiocyanato, isocyano, —NR¹R², (C₁-C₆)alkanoyloxy, (C₁-C₆)alkoxy, phenyloxy, (C₁-C₆)alkylthio, (C₁-C₆)alkylsulfonyl or phenylthio;

wherein R¹ and R² are independently hydrogen, cyano, (C₁-C₆)alkyl, halo(C₁-C₆)alkyl, cyano(C₁-C₆)alkyl, phenyl(C₁-C₆)alkyl, (C₃-C₆)alkenyl, halo(C₃-C₆)alkenyl, (C₃-C₆)alkynyl, phenyl, halophenyl, formyl, (C₁-C₆)alkylcarbonyl, halo(C₁-C₆)alkylcarbonyl, (C₂-C₆)alkenylcarbonyl, halo(C₂-C₆)alkenylcarbonyl, (C₁-C₆)alkoxy(C₁-C₆)alkylcarbonyl, phenylcarbonyl, phenyl(C₂-C₆)alkenylcarbonyl, carboxy, (C₁-C₆)alkoxycarbonyl, halo(C₁-C₆)alkoxycarbonyl, cyano(C₁-C₆)alkoxycarbonyl, (C₂-C₆)alkenyloxycarbonyl, (C₃-C₆)alkynyloxycarbonyl, (C₁-C₆)alkanoyl(C₁-C₆)alkoxycarbonyl, (C₁-C₆)alkoxycarbonyl(C₁-C₆)alkoxycarbonyl, carboxy(C₁-C₆)alkoxycarbonyl, phenyloxycarbonyl, phenyl(C₁-C₆)alkoxycarbonyl, ((C₁-C₆)alkylthio)carbonyl, N-(C₁-C₆)alkylaminocarbonyl, N,N-di(C₁-C₆)alkylaminocarbonyl, N-phenyl-N-(C₁-C₆)alkylaminocarbonyl, N-(phenylcarbonyl)aminocarbonyl, di(C₁-C₆)alkylphosphoryl, (C₁-C₆)alkylsulfonyl, (C₂-C₆)alkenylsulfonyl, N,N-di(C₁-C₆)alkylaminosulfonyl, phenylsulfonyl, pyridyl or pyrazinyl; or R¹ and R² together with the nitrogen to which they are attached may form a 5- or 6-membered ring selected from 2-oxazolidonyl, pyrrolidinonyl, piperidonyl and succinimidyl; and Z₁ is hydrogen or (C₁-C₆)alkyl;
Z₂ is hydrogen or (C₁-C₆)alkyl;
Z₃ is hydrogen or (C₁-C₆)alkyl; and
agronomically acceptable salts thereof.

In one embodiment of the invention are compounds of the formula

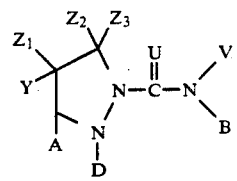

(I)

wherein

A and B are pyridyl, furyl, thiazolyl or naphthyl, each of which is optionally substituted by one or two independently chosen substituents selected from nitro, (C₁-C₆)alkyl, halo(C₁-C₆)alkyl and halo;

phenyl or phenyl substituted by one to three substituents independently selected from (C₁-C₆)alkyl, halo(C₁-C₆)alkyl, halo, (C₁-C₆)alkoxy, halo(C₁-C₆)alkoxy, (C₃-C₆)alkenyloxy, (C₃-C₆)alkynyloxy, (C₁-C₆)alkoxy(C₁-C₆)alkoxy, phenyl(C₁-C₆)alkoxy, phenyloxy, pyridyloxy, mono(C₁-C₆)alkylaminocarbonyloxy, di(C₁-C₆)alkylaminocarbonyloxy, (C₁-C₆)alkanoyloxy, (C₁-C₆)alkoxycarbonyloxy, (C₁-C₆)alkylsulfonyloxy, (C₁-C₆)alkylthio, halo(C₁-C₆)alkylthio, (C₁-C₆)alkoxy(C₁-C₆)alkyl, (C₁-C₆)alkanoyl, (C₁-C₆)alkoxycarbonyl, nitro, (C₁-C₆)alkylsulfonyl, halo(C₁-C₆)alkylsulfonyl, phenyl, hydroxy, cyano, isocyano, amino, mono(C₁-C₆)alkylamino, di(C₁-C₆)alkylamino, formylamino, (C₁-C₆)alkanoylamino, halo(C₁-C₆)alkanoylamino, phenylcarbonylamino, mono(C₁-C₆)alkylaminocarbonylamino, and di(C₁-C₆)alkylaminocarbonylamino;

U is oxygen or sulfur;

V is hydrogen, (C₁-C₆)alkyl, (C₁-C₆)alkoxy(C₁-C₆)alkyl, formyl, (C₁-C₆)alkylcarbonyl, (C₁-C₆)alkylaminocarbonyl, (C₁-C₆)alkoxycarbonyl, (C₃-C₆)alkenyloxycarbonyl, phenyloxycarbonyl, (C₁-C₆)alkoxycarbonylcarbonyl, cyano(C₁-C₆)alkylthio, (C₁-C₆)alkylthio, phenylthio, (C₁-C₆)alkoxycarbonyl(C₁-C₆)alkylthio or (C₁-C₆)alkoxycarbonylthio;

D is hydrogen, (C₁-C₆)alkoxycarbonyl, (C₁-C₆)alkylsulfonyl, (C₁-C₆)alkylcarbonyl or (C₁-C₆)alkyl;

Y is phenyl, halophenyl, (C₁-C₆)alkyl, halo(C₁-C₆)alkyl, hydroxy(C₁-C₆)alkyl, (C₁-C₆)alkoxy(C₁-C₆)alkyl, (C₁-C₆)alkoxy(C₁-C₆)alkoxy(C₁-C₆)alkyl, (C₁-C₆)alkylcarbonyloxy(C₁-C₆)alkyl, ((C₁-C₆)alkylthio)(C₁-C₆)alkyl, (C₁-C₆)alkylsulfinyl(C₁-C₆)alkyl, cyano(C₁-C₆)alkyl, carboxy(C₁-C₆)alkyl, (C₁-C₆)alkoxycarbonyl(C₁-C₆)alkyl, (C₂-C₆)alkenyl, halo(C₂-C₆)alkenyl, formyl, (C₁-C₆)alkylcarbonyl, halo(C₁-C₆)alkylcarbonyl, phenylcarbonyl, (C₁-C₆)alkoxycarbonylcarbonyl, halocarbonyl, aminocarbonyl, N-(C₁-C₆)alkylaminocarbonyl, N,N-di(C₁-C₆)alkylaminocarbonyl, pyrrolidin-1-ylcarbonyl, piperidin-1-ylcarbonyl, morpholin-1-ylcarbonyl, pyrazol-1-ylcarbonyl, imidazol-1-ylcarbonyl, pyrrol-1-ylcarbonyl, hydroxy(C₁-C₆)alkylaminocarbonyl, thio(C₁-C₆)alkylaminocarbonyl, phenylaminocarbonyl, carboxy, (C₁-C₆)alkoxycarbonyl, (C₁-C₆)alkoxy(C₁-C₆)alkoxycarbonyl, (C₁-C₆)alkoxy(C₁-C₆)alkoxy(C₁-C₆)alkoxycarbonyl, halo(C₁-C₆)alkoxycarbonyl, cyano(C₁-C₆)alkoxycarbonyl, (C₁-C₆)alkylthio(C₁-C₆)alkoxycarbonyl, ((C₁-C₆)alkylthio)thiocarbonyl, pyridyl, oxazol-2-yl, 2-benzoxazolyl, isothiocyanato, isocyano, —NR¹R², (C₁-C₆)alkanoyloxy, (C₁-C₆)alkoxy, phenyloxy, (C₁-C₆)alkylthio, (C₁-C₆)alkylsulfonyl or phenylthio;

wherein R¹ and R² are independently hydrogen, cyano, (C₁-C₆)alkyl, halo(C₁-C₆)alkyl, cyano(C₁-C₆)alkyl, phenyl(C₁-C₆)alkyl, (C₃-C₆)alkenyl, halo(C₃-C₆)alkenyl, (C₃-C₆)alkynyl, phenyl, halophenyl, formyl, ($C_1$-$C_6$)alkylcarbonyl, halo($C_1$-$C_6$)alkylcarbonyl, ($C_2$-$C_6$)alkenylcarbonyl, halo($C_2$-$C_6$)alkenylcarbonyl, ($C_1$-$C_6$)alkoxy($C_1$-$C_6$)alkylcarbonyl, phenylcarbonyl, phenyl($C_2$-$C_6$)alkenylcarbonyl, carboxy, ($C_1$-$C_6$)alkoxycarbonyl, halo($C_1$-$C_6$)alkoxycarbonyl, cyano($C_1$-$C_6$)alkoxycarbonyl, ($C_2$-$C_6$)alkenyloxycarbonyl, ($C_3$-$C_6$)alkynyloxycarbonyl, ($C_1$-$C_6$)alkanoyl($C_1$-$C_6$)alkoxycarbonyl, ($C_1$-$C_6$)alkoxycarbonyl($C_1$-$C_6$)alkoxycarbonyl, carboxy($C_1$-$C_6$)alkoxycarbonyl, phenyloxycarbonyl, phenyl($C_1$-$C_6$)alkoxycarbonyl, (($C_1$-$C_6$)alkylthio)carbonyl, N-($C_1$-$C_6$)alkylaminocarbonyl, N,N-di($C_1$-$C_6$)alkylaminocarbonyl, N-phenyl-N-($C_1$-$C_6$)alkylaminocarbonyl, N-(phenylcarbonyl)aminocarbonyl, di($C_1$-$C_6$)alkylphosphoryl, ($C_1$-$C_6$)alkylsulfonyl, ($C_2$-$C_6$)alkenylsulfonyl, N,N-di($C_1$-$C_6$)alkylaminosulfonyl, phenylsulfonyl, pyridyl or pyrazinyl; or $R^1$ and $R^2$ together with the nitrogen to which they are attached may form a 5- or 6-membered ring selected from 2-oxazolidonyl, pyrrolidinonyl, piperidonyl and succinimidyl; and $Z_1$ is hydrogen or ($C_1$-$C_6$)alkyl;
$Z_2$ is hydrogen or ($C_1$-$C_6$)alkyl;
$Z_3$ is hydrogen or ($C_1$-$C_6$)alkyl; and
agronomically acceptable salts thereof.

Preferred compounds of this embodiment are compounds of the formula

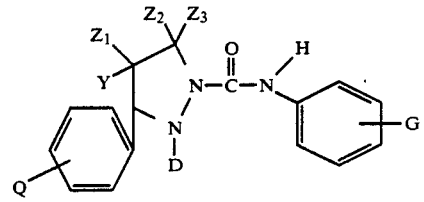

wherein
Q is hydrogen, halo, hydroxy, halo($C_1$-$C_6$)alkyloxy or ($C_1$-$C_6$)alkoxy;

G is halo, halo($C_1$-$C_6$)alkyl, ($C_1$-$C_6$)alkoxycarbonyl or halo($C_1$-$C_6$)alkoxy;

D is hydrogen, phenylcarbonyl, halophenylcarbonyl, phenylsulfonyl, halophenylsulfonyl, ($C_1$-$C_6$)alkylsulfonyl, ($C_1$-$C_6$)alkanoyl, halo($C_1$-$C_6$)alkanoyl, ($C_1$-$C_6$)alkoxycarbonyl or ($C_1$-$C_6$)alkyl;

Y is hydrogen, ($C_1$-$C_6$)alkylaminocarbonyl, phenyl, halophenyl, ($C_1$-$C_6$)alkoxycarbonylamino or ($C_1$-$C_6$)alkoxycarbonyl(($C_1$-$C_6$)alkyl)amino;

$Z_1$ is hydrogen or ($C_1$-$C_6$)alkyl; and
$Z_2$ and $Z_3$ are hydrogen.

More preferred are compounds of the embodiment wherein Q is hydrogen, 4-halo, 4-($C_1$-$C_6$)alkoxy or 4-halo($C_1$-$C_6$)alkoxy;

G is 4-halo, 4-halo($C_1$-$C_6$)alkyl or 4-halo($C_1$-$C_6$)alkoxy; and

Y is hydrogen, ($C_1$-$C_6$)alkylaminocarbonyl, phenyl, 4-halophenyl, ($C_1$-$C_6$)alkoxycarbonylamino or ($C_1$-$C_6$)alkoxycarbonyl(($C_1$-$C_6$)alkyl)amino.

Most preferred are compounds wherein
Q is 4-chloro, G is 4-trifluoromethyl, D is hydrogen, 4-chlorophenylcarbonyl, 4-chlorophenylsulfonyl, methoylsulfonyl, acetyl, chloroacetyl, methoxycarbonyl or methyl, $Z_1$ is hydrogen and Y is phenyl;

Q is 4-chloro, G is 4-trifluoromethyl, D is hydrogen, $Z_1$ is methyl and Y is phenyl, hydrogen or methylaminocarbonyl;

Q is 4-chloro, G is 4-trifluoromethyl, Y is 4-chlorophenyl, $Z_1$ is hydrogen and D is hydrogen, methoxycarbonylcarbonyl, chloroacetyl or 2-bromoethylcarbonyl;

Q is 4-propoxy, G is 4-trifluoromethyl, Y is methoxycarbonyl(methyl)amino, $Z_1$ is hydrogen and D is hydrogen; or Q is 4-chloro, G is 4-trifluoromethoxy, $Z_1$ and D are hydrogen and Y is methoxycarbonylamino or methoxycarbonyl(methyl)amino.

In another embodiment of the invention are compounds of the formula

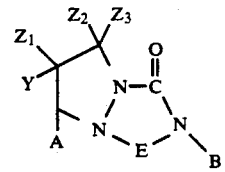

wherein
A and B are pyridyl, furyl, thiazolyl or naphthyl, each of which is optionally substituted by one or two independently chosen substituents selected from nitro, ($C_1$-$C_6$)alkyl, halo($C_1$-$C_6$)alkyl and halo;

phenyl or phenyl substituted by one to three substituents independently selected from ($C_1$-$C_6$)alkyl, halo($C_1$-$C_6$)alkyl, halo, ($C_1$-$C_6$)alkoxy, halo($C_1$-$C_6$)alkoxy, ($C_3$-$C_6$)alkenyloxy, ($C_3$-$C_6$)alkynyloxy, ($C_1$-$C_6$)alkoxy($C_1$-$C_6$)alkoxy, phenyl($C_1$-$C_6$)alkoxy, phenyloxy, pyridyloxy, mono($C_1$-$C_6$)alkylaminocarbonyloxy, di($C_1$-$C_6$)alkylaminocarbonyloxy, ($C_1$-$C_6$)alkanoyloxy, ($C_1$-$C_6$)alkoxycarbonyloxy, ($C_1$-$C_6$)alkylsulfonyloxy, ($C_1$-$C_6$)alkylthio, halo($C_1$-$C_6$)alkylthio, ($C_1$-$C_6$)alkoxy($C_1$-$C_6$)alkyl, ($C_1$-$C_6$)alkanoyl, ($C_1$-$C_6$)alkoxycarbonyl, nitro, ($C_1$-$C_6$)alkylsulfonyl, halo($C_1$-$C_6$)alkylsulfonyl, phenyl, hydroxy, cyano, isocyano, amino, mono($C_1$-$C_6$)alkylamino, di($C_1$-$C_6$)alkylamino, formylamino, ($C_1$-$C_6$)alkanoylamino, halo($C_1$-$C_6$)alkanoylamino, phenylcarbonylamino, mono($C_1$-$C_6$)alkylaminocarbonylamino, and di($C_1$-$C_6$)alkylaminocarbonylamino;

U is oxygen or sulfur;
E is ($C_1$-$C_6$)alkylidene, carbonyl, dicarbonyl or carbonyl($C_1$-$C_6$)alkylidene;
Y is phenyl, halophenyl, ($C_1$-$C_6$)alkyl, halo($C_1$-$C_6$)alkyl, hydroxy($C_1$-$C_6$)alkyl, ($C_1$-$C_6$)alkoxy($C_1$-$C_6$)alkyl, ($C_1$-$C_6$)alkoxy($C_1$-$C_6$)alkoxy($C_1$-$C_6$)alkyl, ($C_1$-$C_6$)alkylcarbonyloxy($C_1$-$C_6$)alkyl, (($C_1$-$C_6$)alkylthio)($C_1$-$C_6$)alkyl, ($C_1$-$C_6$)alkylsulfinyl($C_1$-$C_6$)alkyl, cyano($C_1$-$C_6$)alkyl, carboxy($C_1$-$C_6$)alkyl, ($C_1$-$C_6$)alkoxycarbonyl($C_1$-$C_6$)alkyl, ($C_2$-$C_6$)alkenyl, halo($C_2$-$C_6$)alkenyl, formyl, ($C_1$-$C_6$)alkylcarbonyl, halo($C_1$-$C_6$)alkylcarbonyl, phenylcarbonyl, ($C_1$-$C_6$)alkoxycarbonylcarbonyl, halocarbonyl, aminocarbonyl, N-($C_1$-$C_6$)alkylaminocarbonyl, N,N-di($C_1$-$C_6$)alkylaminocarbonyl, pyrrolidin-1-ylcarbonyl, piperidin-1-ylcarbonyl, morpholin-1-ylcarbonyl, pyrazol-1-ylcarbonyl, imidazol-1-ylcarbonyl, pyrrol-1-ylcarbonyl, hydroxy($C_1$-$C_6$)alkylaminocarbonyl, thio($C_1$-$C_6$)alkylaminocarbonyl, phenylaminocarbonyl, carboxy, ($C_1$-$C_6$)alkoxycarbonyl, ($C_1$-$C_6$)alkoxy($C_1$-$C_6$)alkoxycarbonyl, ($C_1$-$C_6$)alkoxy($C_1$-$C_6$)alkoxy($C_1$-$C_6$)alkoxycarbonyl, halo($C_1$-$C_6$)alkoxycarbonyl, cyano($C_1$-$C_6$)alkoxycarbonyl, ($C_1$-$C_6$)alkylthio($C_1$-$C_6$)alkoxycarbonyl, (($C_1$-$C_6$)alkylthio)thiocarbonyl, pyridyl, oxazol-2-yl, 2-benzoxazolyl, isothiocyanato, isocyano, —$NR^1R^2$, ($C_1$-$C_6$)alkanoyloxy, ($C_1$-$C_6$)alkoxy, phenyloxy, ($C_1$-$C_6$)alkylthio, ($C_1$-$C_6$)alkylsulfonyl or phenylthio;

wherein $R^1$ and $R^2$ are independently hydrogen, cyano. $(C_1-C_6)$alkyl, halo$(C_1-C_6)$alkyl, cyano$(C_1-C_6)$alkyl, phenyl$(C_1-C_6)$alkyl, $(C_3-C_6)$alkenyl, halo$(C_3-C_6)$alkenyl, $(C_3-C_6)$alkynyl, phenyl, halophenyl, formyl, $(C_1-C_6)$alkylcarbonyl, halo$(C_1-C_6)$alkylcarbonyl, $(C_2-C_6)$alkenylcarbonyl, halo$(C_2-C_6)$alkenylcarbonyl, $(C_1-C_6)$alkoxy$(C_1-C_6)$alkylcarbonyl, phenylcarbonyl, phenyl$(C_2-C_6)$alkenylcarbonyl, carboxy, $(C_1-C_6)$alkoxycarbonyl, halo$(C_1-C_6)$alkoxycarbonyl, cyano$(C_1-C_6)$alkoxycarbonyl, $(C_2-C_6)$alkenyloxycarbonyl, $(C_3-C_6)$alkynyloxycarbonyl, $(C_1-C_6)$alkanoyl$(C_1-C_6)$alkoxycarbonyl, $(C_1-C_6)$alkoxycarbonyl$(C_1-C_6)$alkoxycarbonyl, carboxy$(C_1-C_6)$alkoxycarbonyl, phenyloxycarbonyl, phenyl$(C_1-C_6)$alkoxycarbonyl, $((C_1-C_6)$alkylthio)carbonyl, N-$(C_1-C_6)$alkylaminocarbonyl, N,N-di$(C_1-C_6)$alkylaminocarbonyl, N-phenyl-N-$(C_1-C_6)$alkylaminocarbonyl, N-(phenylcarbonyl)aminocarbonyl, di$(C_1-C_6)$alkylphosphoryl, $(C_1-C_6)$alkylsulfonyl, $(C_2-C_6)$alkenylsulfonyl, N,N-di$(C_1-C_6)$alkylaminosulfonyl, phenylsulfonyl, pyridyl or pyrazinyl; or $R^1$ and $R^2$ together with the nitrogen to which they are attached may form a 5- or 6-membered ring selected from 2-oxazolidonyl, pyrrolidinonyl, piperidonyl and succinimidyl; and $Z_1$ is hydrogen or $(C_1-C_6)$alkyl;
$Z_2$ is hydrogen or $(C_1-C_6)$alkyl;
$Z_3$ is hydrogen or $(C_1-C_6)$alkyl; and
agronomically acceptable salts thereof.

Preferred compounds of the embodiment are compounds of the formula

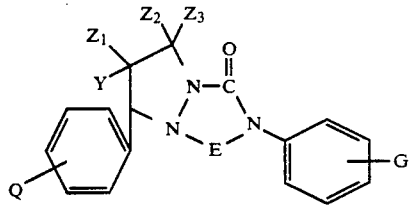

wherein
Q is hydrogen, halo, hydroxy, halo$(C_1-C_6)$alkyloxy or $(C_1-C_6)$alkoxy;
G is halo, halo$(C_1-C_6)$alkyl, $(C_1-C_6)$alkoxycarbonyl or halo$(C_1-C_6)$alkoxy;
E is $(C_1-C_6)$alkylidene, carbonyl, dicarbonyl or carbonyl$(C_1-C_6)$alkylidene;
Y is hydrogen, $(C_1-C_6)$alkylaminocarbonyl, phenyl or halophenyl;

$Z_1$ is hydrogen or $(C_1-C_6)$alkyl; and
$Z_2$ and $Z_3$ are hydrogen.

More preferred are compounds of the embodiment wherein Q is hydrogen, 4-halo, 4-$(C_1-C_6)$alkoxy or 4-halo$(C_1-C_6)$alkoxy;
G is 4-halo, 4-halo$(C_1-C_6)$alkyl or 4-halo$(C_1-C_6)$alkoxy; and
Y is hydrogen, phenyl or 4-halophenyl.

Most preferred are compounds wherein
Q is 4-chloro, G is 4-trifluoromethyl, $Z_1$ is hydrogen, Y is phenyl and E is methylene, methylmethylene, carbonyl, dicarbonyl or carbonylmethylene;
Q is 4-chloro, G is 4-trifluoromethyl, $Z_1$ is methyl, Y is hydrogen, and E is carbonyl; or
Q is 4-chloro, G is 4-trifluoromethyl, Y is 4-chlorophenyl, $Z_1$ is hydrogen and E is dicarbonyl or carbonylmethylene.

Processes for preparing the starting compounds for the compounds of the invention are disclosed in the literature, for example, U.S. Pat. Nos. 4,863,947 and 4,156,007 incorporated herein by reference.

Further, in the case where Y is attached to the pyrazoline ring by a nitrogen, the compounds of this invention are prepared from compounds made from the compounds disclosed in U.S. Pat. Nos. 4,863,947 according to the following general synthesis shown in Scheme 1. More particularly, the starting pyrazoline (III) (wherein R is alkyl and A, B, U, V and Z are as defined above) contains a carboxylic acid ester at the Y-position. The ester is saponified to yield the corresponding carboxylic acid (IV) under normal saponification conditions. Preferred solvents are protic solvents such as methanol or solvent mixtures such as methanol and tetrahydrofuran at temperatures between about 0° C. and about 100° C., more preferably between about 25° C. and about 75° C.

The acid is then converted to the acid chloride (V) by known means, for example, treatment with thionyl chloride. Preferred solvents are toluene and chloroform.

The acid chloride is reacted with azide anion, for example, sodium azide, to yield the azidocarbonyl compound (VI). Preferred solvents are acetonitrile and dimethylformamide.

The azidocarbonyl compound is then converted to the corresponding isocyanate (VII) by heating in an appropriate solvent until gas evolution ceases. Preferred solvents are toluene, benzene, and chlorobenzene.

Scheme 1

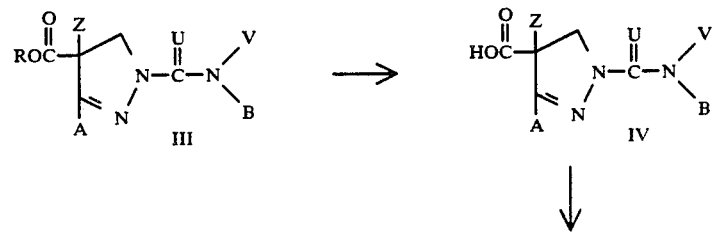

Scheme 1

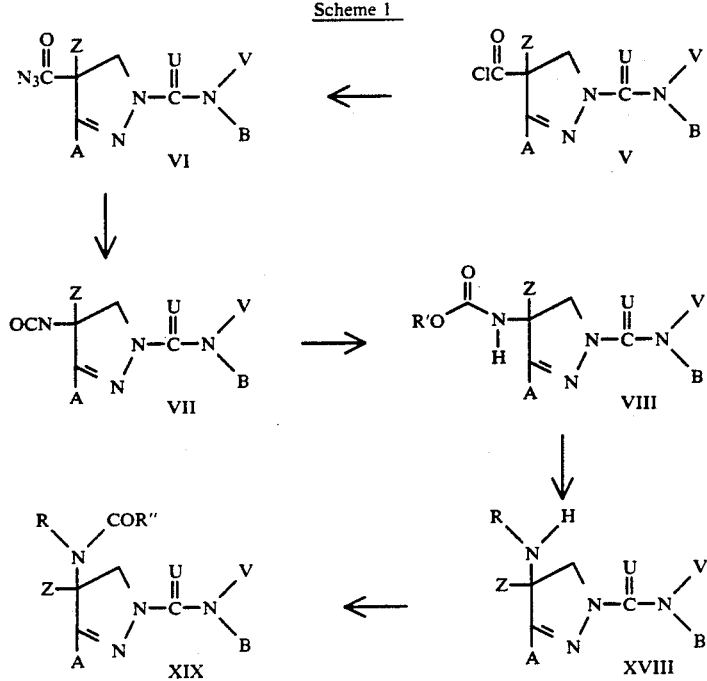

The carboalkoxyamino compounds of the invention (VIII) are obtained by reacting the isocyanato compounds with the appropriate alcohol. The alcohol can be used as the solvent, for example methanol or ethanol, or alternatively a slight excess of the alcohol along with a base is used in a inert solvent. Preferred solvents are benzene and toluene.

In the case where the compound (VIII) is a t-butyloxycarbonylamino compound and the like, the carboalkoxyamino compound can then be decarbalkoxylated to yield the corresponding amino compound (IX) by heating in an inert solvent in the presence of acid. Preferred solvents include halogenated solvents such as chloroform and methylene chloride. Preferred acids include, for example, trifluoroacetic acid and toluene sulfonic acid.

The corresponding carboxamide compounds (X), and the like, are prepared from the amino compound by treatment with the appropriate acid chloride in the presence of base. Preferred solvents are methylene chloride and tetrahydrofuran. Prefered bases include pyridine and triethylamine.

Alternatively, the amino-substituted compounds are prepared using the synthesis shown in Scheme 2.

Scheme 2

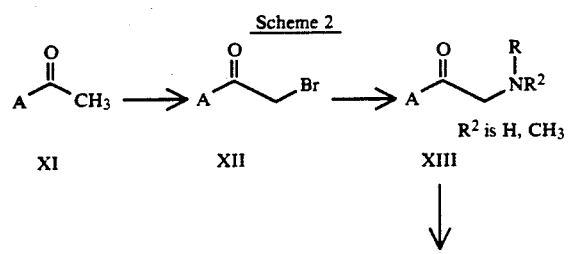

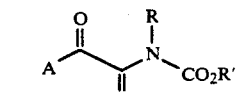
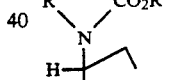
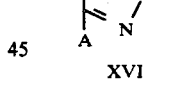

More particularly, a methyl ketone (XI) is brominated using conditions known in the art. The bromo compound (XII) is reacted with a mono- or di-alkylamine under known conditions to obtain the resulting alkylaminomethyl ketone (XIII). The reaction is typically carried out at a temperature between about −50° C. and 20° C. in a nonprotic solvent, for example, methylene chloride.

The alkylaminomethyl ketone is reacted with, for example, an alkyl chloroformate, to produce the substituted carbamate (XIV). Preferred solvents are aprotic solvents such as methylene chloride at a temperature between about −25° C. and about 50° C., more preferably between about 0° C. and about 20° C.

The carbamate is then treated with formaldehyde to obtain the corresponding prop-2-enone (XV). Preferred solvents are protic solvents such as propanol or 2-methoxyethanol at temperatures between about 0° C. and about 140° C., preferably at about the reflux temperature of the solvent used. Preferably, catalytic amounts, a base such as piperidine and an acid such as acetic acid are also present in the reaction mixture.

The resulting prop-2-enone is then converted to the corresponding dihydropyrazole (XVI) by treatment with hydrazine. Preferred solvents are protic solvents such as methanol at temperatures between about 0° C. and about 100° C., preferably between about 25° C. and about 70° C. The resulting dihydropyrazole is generally reacted with an appropriate isocyanate as described in U.S. Pat. No. 4,863,947 to obtain the corresponding carboxamide (XVII).

The carboxamide (XVII) can be decarboxylated by known means to obtain the disubstituted amino compound (XVIII). Preferred, when R' is 2,2,2-trichloroethoxycarbonyl, are reagents such as acetic acid and zinc dust in protic solvents such as methanol at temperatures from about 0° C. to about 100° C., more preferably from about 20° C. to about 70° C.

The disubstituted amino dihydropyrazole is then acylated under standard conditions to yield the corresponding acylated amino compound XIX. Preferred solvents are aprotic solvents such as ethyl acetate at temperatures between about −25° C. and about 50° C., more preferably between about 0° C. and about 20° C.

The corresponding oxygen and sulfur compounds are prepared as shown in Schemes 3, 4, 5, and 6 starting from the halomethylketone XII which is alkoxylated or alkylthiolated under known conditions to yield the corresponding oxygen (XX, XXIV) or sulfur (XXIX) compounds. The sulfur is optionally oxidized to the corresponding sulfone using standard conditions and reagents. Preferably, oxidizing agents such as peracetic acid or m-chloroperbenzoic acid are used in aprotic solvents such as methylene chloride at temperatures between about −50° C. and about 50° C., more preferably between about −10° C. and about 10° C. These keto compounds are then converted to compounds of the invention using the steps analagous to the preparation of the amino compounds discussed above.

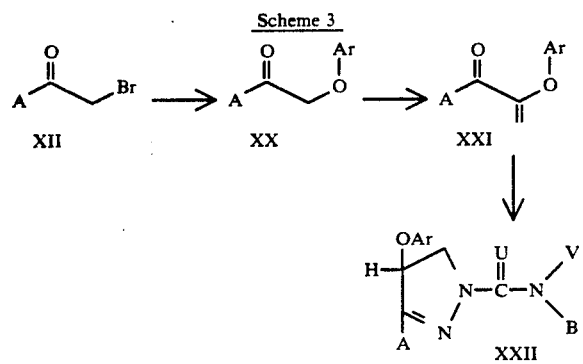

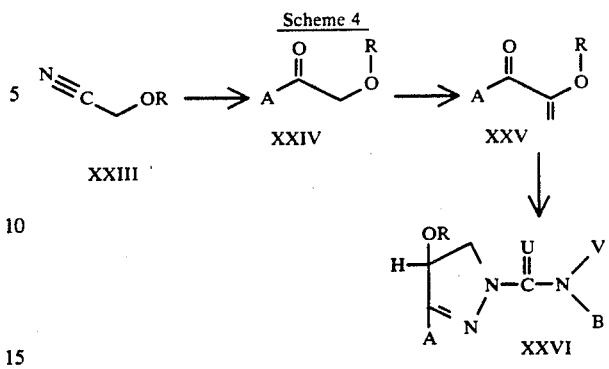

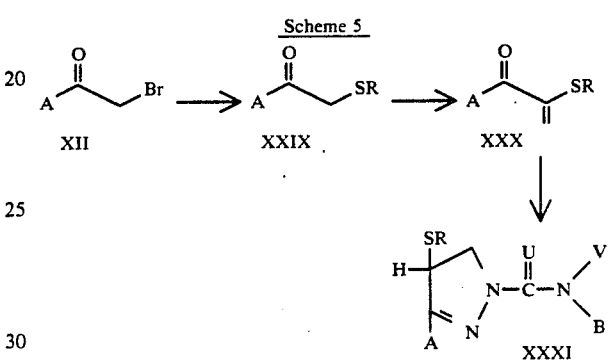

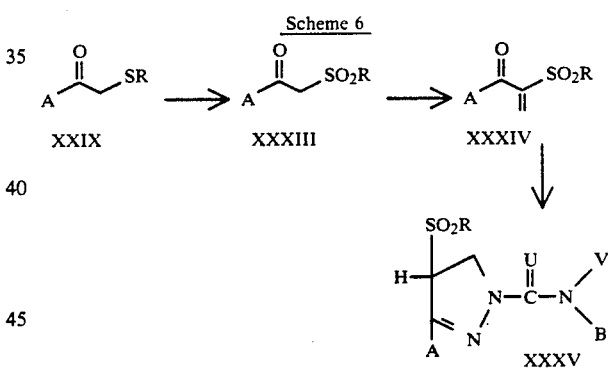

The compounds of the instant invention are prepared from any one of the dihydropyrazoles discussed above by reducing the dihydropyrazole to a 2,3,4,5-tetrahydropyrazole in the presence of a reducing agent such as diisobutylaluminum hydride (DBAL-H). The reduction is carried out in a nonprotic solvent, for example tetrahydrofuran, dioxane, diethylether, glyme, diglyme or benzene. Preferably, the reaction is carried out in tetrahydrofuran. Generally the reaction is carried out between from about −75° C. to about 100° C., preferably from about −20° C. to about 50° C.

Additional compounds of the invention are prepared by replacing the hydrogen of the nitrogen at the 2-position with the appropriate acyl or alkyl group by methods known to one skilled in the art, for example, reaction with the appropriate acid chloride, sulfonyl chloride or halo compound.

The compounds of the invention wherein E is alkylidene, carbonyl or dicarbonyl are prepared by means known to one skilled in the art by treating the appropriate tetrahydro compound wherein D is hydrogen with the appropriate aldehyde such as formalin or acetaldehyde or acid chloride such as oxalyl chloride.

The compounds of the invention wherein E is carbonylalkylidene are prepared by treating the compound of the invention wherein D is haloalkylcarbonyl with base such as sodium hydride in an aprotic solvent.

The following examples will further illustrate this invention but are not intended to limit it in any way. In Tables I and II, typical 1-substituted-4-substituted-2,3,4,5-tetrahydro-1H-pyrazoles of the present invention are listed. Structures were confirmed by NMR and in some cases by IR and/or elemental analysis. Table III contains NMR data for those examples which were oils. Specific illustrative preparations of compounds of the invention are described. It will be appreciated by those skilled in the art that the Y and Z substituents can be interchanged without departing from the spirit or scope of the present invention.

TABLE I

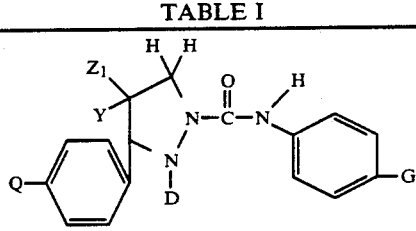

| Cmpd No. | Y | $Z_1$ | D | Q | G | mp °C. |
|---|---|---|---|---|---|---|
| 1. | H-cis | $CH_3$ | H | Cl | $CF_3$ | 186–188 |
| 2. | H-trans | $CH_3$ | H | Cl | $CF_3$ | 131–133 |
| 3. | $C_6H_5$ | H | H | Cl | $CF_3$ | 212–214 |
| 4. | $C_6H_5$ | H | $CH_3$ | Cl | $CF_3$ | 145–147 |
| 5. | $C_6H_5$ | H | $CH_2CH_3$ | Cl | $CF_3$ | foam |
| 6. | $C_6H_5$ | H | $COC_6H_4Cl$ | Cl | $CF_3$ | 181–183 |
| 7. | $C_6H_5$ | H | $COCH_3$ | Cl | $CF_3$ | 186–189 |
| 8. | $C_6H_5$ | H | $COCH_2Cl$ | Cl | $CF_3$ | 204–207 |
| 9. | $C_6H_5$ | H | $CO_2CH_3$ | Cl | $CF_3$ | 171–173 |
| 10. | $C_6H_5$ | H | $SO_2C_6H_5Cl$ | Cl | $CF_3$ | 151–154 |
| 11. | $C_6H_5$ | H | $SO_2CH_3$ | Cl | $CF_3$ | 140–142 |
| 12. | $C_6H_5$ | $CH_3$ | H | Cl | $CF_3$ | 226–229 |
| 13. | $C_6H_4$—4Cl | H | H | Cl | $CF_3$ | 240–243 |
| 14. | $C_6H_4$—4Cl | H | $COCH_2Cl$ | Cl | $CF_3$ | 180–182 |
| 15. | $C_6H_4$—4Cl | H | $COCH_2CH_2Br$ | Cl | $CF_3$ | 155–157 |
| 16. | $C_6H_4$—4Cl | H | $COCO_2CH_3$ | Cl | $CF_3$ | 126–129 |
| 17. | $NHCO_2CH_3$ | H | H | Cl | $OCF_3$ | 179–181 |
| 18. | $N(CH_3)CO_2CH_3$ | H | H | Cl | $OCF_3$ | 107–114 |
| 19. | $N(CH_3)CO_2CH_3$ | H | H | $O(CH_2)_2CH_3$ | $OCF_3$ | oil |
| 20. | $CONHCH_3$ | $CH_3$ | H | Cl | $CF_3$ | 202–204 |

TABLE II

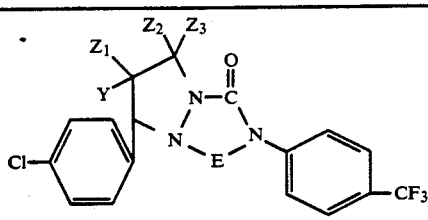

| Cmpd No. | Y | $Z_1$ | E | $Z_2$ | $Z_3$ | mp °C. |
|---|---|---|---|---|---|---|
| 21. | H-cis | $CH_3$ | —CO— | H | H | 152–155 |
| 22. | $C_6H_5$ | H | —$CH_2$— | H | H | 184–187 |
| 23. | $C_6H_5$ | H | —$CHCH_3$— | H | H | 103–105 |
| 24. | $C_6H_5$ | H | —CO— | H | H | 148–150 |
| 25. | $C_6H_5$ | H | —COCO— | H | H | 125–128 |
| 26. | $C_6H_5$ | H | —$COCH_2$— | H | H | 214–216 |
| 27. | $C_6H_4$—4Cl | H | —COCO— | H | H | 283–286 |

TABLE II-continued

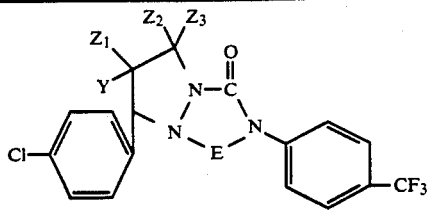

| Cmpd No. | Y | $Z_1$ | E | $Z_2$ | $Z_3$ | mp °C. |
|---|---|---|---|---|---|---|
| 28. | $C_6H_4$—4Cl | H | —$COCH_2$— | H | H | 231–233 |

EXPERIMENTAL

EXAMPLES 1 AND 2 cis-N-(4-trifluoromethylphenyl)-3-(4-chlorophenyl)-4-methyl-2,3,4,5-tetrahydro-1H-pyrazole-1-carboxamide
and
trans-N-(4-trifluoromethylphenyl)-3-(4-chlorophenyl)-4-methyl-2,3,4,5-tetrahydro-1H-pyrazole-1-carboxamide To 15.3 grams (g) (40 millimole(mmole)) of N-(4-trifluoromethylphenyl)-3-(4-chlorophenyl)-4-methyl-4,5-dihydro-1H-pyrazole-1-carboxamide (prepared following the procedure of Example 2 in U.S. Pat. No. 4,156,007 and using 4-trifluoromethylphenylisocyanate in place of 4-chlorophenylisocyanate in the final step) in 100 ml of tetrahydrofuran (THF) that had been cooled under a nitrogen atmosphere to −75° C. was added 59 ml (88 mmole) of 1.5M diisobutylaluminum hydride (DIBAL-H) in toluene. The reaction mixture was warmed to 0° C. and stirred for 1 hour. The mixture was carefully quenched with 40 ml of methanol. This mixture was poured onto a mixture of 300 g of ice and 75 ml of 12M aqueous hydrochloric acid. The mixture was extracted with ethyl acetate. The organic layer was dried over anhydrous magnesium sulfate, filtered and concentrated in vacuo. The resulting mixture was chromatographed over silica gel using diethyl ether and hexanes and crystalized from ethanol to give predominately the cis isomer, mp 186°–188° C. NMR(200 MHz, CDCl$_3$) 0.8 d 3H, 2.9 septet 1H, 3.3 dd 1H, 4.1 dd 1H, 4.4 dd 1H, 4.7 d 1H, 7.2 abq 4H, 7.6 abq 4H, 8.5 bs 1H; and to a lesser extent the trans isomer mp 131°–133° C. NMR(200 MHz, CDCl$_3$) 1.2 d 3H, 2.4 septet 1H, 3.5 t 1H, 3.7 t 1H, 3.9 t 1H, 4.3 d 1H, 7.3 abq 4H, 7.6 abq 4H, 8.5 bs 1H.

EXAMPLE 3

N-(4-trifluoromethylphenyl)-3-(4-chlorophenyl)-4-phenyl-2,3,4,5-tetrahydro-1H-pyrazole-1-carboxamide To 20.2 g (45 mmole) of N-(4-trifluoromethylphenyl)-3-(4-chlorophenyl)-4-phenyl-4,5-dihydro-1H-pyrazole-1-carboxamide U.S. Pat. No. 4,156,007, column 7, line 17) in 75 ml of tetrahydrofuran (THF) that had been cooled under a nitrogen atmosphere to −75° C. was added 100 ml of 1.0M diisobutylaluminum hydride (DIBAL-H) in THF. The reaction mixture was warmed to 0° C. and stirred for 1 hour. An additional 50 ml of the 1.0M DIBAL-H solution was added and the reaction was warmed to 20° C. After 1 more hour yet another 50 ml of the 1.0M DIBAL-H solution was added. After stirring at 20° C. for an additional hour the mixture was cooled to 0° C. and carefully quenched with 40 ml of methanol. This mixture was poured onto a mixture of 300 g of ice and 75 ml of 12M aqueous hydrochloric acid. The mixture was extracted with ethyl acetate. The organic layer was dried over anhydrous magnesium sulfate, filtered and concentrated in vacuo. The resulting solid was recrystallized from 600 ml of ethanol to yield 10.4 g of product, mp 212°–214° C.

Examples 12, 13, and 20 were prepared by following essentially the same procedure and starting from the appropriate dihydropyrazole made by procedures disclosed in U.S. Pat. Nos. 4,156,007 (example 13) and 4,663,341 (examples 12 and 20).

EXAMPLE 5

N-(4-trifluoromethylphenyl)-3-(4-chlorophenyl)-4-phenyl-2-ethyl-2,3,4,5-tetrahydro-1H-pyrazole-1-carboxamide To 1.0 g (2.2 mmole) of N-(4-trifluoromethylphenyl)-3-(4-chlorophenyl)-4-phenyl-2,3,4,5-tetrahydro-1H-pyrazole-1-carboxamide (Example 3) in 5 ml of dimethylformamide was added 0.5 ml (3.0 mmole) of diisopropylethylamine and 0.25 ml (3.0 mmole) of ethyl iodide. The mixture was heated at 60° C. for 18 hours and then partitioned between diethyl ether and water. The organic layer was washed with water and brine and then dried over anhydrous magnesium sulfate. Filtration, concentration in vacuo, and chromatography on silica gel using diethyl ether and hexanes gave the expected compound, a foam. NMR 1.3 t 3H, 3.1 q 2H, 4.1 dd 1H, 4.3 dd 1H, 4.4 t 1H, 6.7 d 2H, 6.9 m 2H, 7.1 m 5H, 7.5 s 4H, 8.4 s 1H.

Example 4 was prepared following essentially the same procedure and using methyl iodide in place of ethyl iodide.

EXAMPLE 8

N-(4-trifluoromethylphenyl)-3-(4-chlorophenyl)-4-phenyl-2-(2-chloroacetyl)-2,3,4,5-tetrahydro-1H-pyrazole-1-carboxamide To 2.0 g (4.5 mmole) of N-(4-trifluoromethylphenyl)-3-(4-chlorophenyl)-4-phenyl-2,3,4,5-tetrahydro-1H-pyrazole-1-carboxamide (Example 3) in 20 ml of ethyl acetate was added 0.4 ml (5.0 mmole) of chloroacetyl chloride. The reaction was stirred for 1 hour and then washed with water and brine and dried over anhydrous magnesium sulfate. The organic layer was concentrated in vacuo and the resulting solid was triturated with ethyl ether/hexanes to yield 2.1 g of white solid, mp 204°–207° C.

Examples 6, 7, 9, 10, 11, 14, 15 and 16 were prepared following essentially the same procedure starting with Example 3 or Example 13 and using the appropriate chloride selected from acetyl chloride, chloroacetylchloride, 3-bromopropionyl chloride, 4-chlorobenzoyl chloride, methyl chloroformate, 4-chlorophenylsulfonyl chloride, methanesulfonyl chloride and methyl oxalyl chloride.

EXAMPLE 17

N-(4-trifluoromethoxyphenyl)-3-(4-chlorophenyl)-4-(N-(methoxycarbonyl)amino)-2,3,4,5-tetrahydro-1H-pyrazole-1-carboxamide a.

2-(N-(methoxycarbonyl)amino)-4'-chloroacetophenone

To a slurry of 30 g (214 mmole) of hexamethylenetetramine in 400 ml of acetonitrile was added 50 g (214 mmole) of 2-bromo-4'-chloroacetophenone in 100 ml of warm acetonitrile, the mixture self warms to 45° C. After stirring for 1 hour the mixture was diluted with diethyl ether and filtered giving a crude quaternary salt which was used directly in the next step.

To a slurry of this crude quaternary salt in 400 ml of ethanol was added 80 ml of 37% aqueous hydrochloric acid. After stirring for 1 hour all was in solution. The resulting mixture was concentrated in vacuo, basified with dilute aqueous sodium hydroxide and extracted with methylene chloride giving a solution of crude 2-amino-4'-chloroacetophenone which was used as is in the next step.

The methylene chloride solution of 2-amino-4'-chloroacetophenone was cooled to 0° C. and 40 g (423 mmole) of methylchloroformate was added along with 60 g of 25% aqueous sodium hydroxide. Separation of the organic layer, drying over anhydrous magnesium sulfate, concentration in vacuo and trituration with diethyl ether and hexanes gave 63 g of the 2-(N-(methoxycarbonylamino)-4'-chloroacetophenone, a white solid. mp 126°–128° C.

b.

N-(4-trifluoromethoxyphenyl)-3-(4-chlorophenyl)-4-(N-(methoxycarbonyl)amino)-2,3,4,5-tetrahydro-1H-pyrazole-1-carboxamide By substantially following the procedure given in Example 19e using 2-(N-(methoxycarbonyl)amino)-4'-chloroacetophenone in place of 2-(N-methyl-N-(methoxycarbonyl)amino)-4'-difluoromethoxyacetophenone and continuing with Example 19f, and Example 19i the expected compound, mp 107°–114° C., was obtained.

EXAMPLE 18

N-(4-trifluoromethoxyphenyl)-3-(4-chlorophenyl)-4-(N-methyl-N-(methoxycarbonyl)amino)-2,3,4,5-tetrahydro-1H-pyrazole-1-carboxamide By substantially following the procedure given in Example 19dii and substituting 2-bromo-4'-chloroacetophenone for 2-bromo-4'-difluoromethoxyacetophenone, and continuing with Example 19e, Example 19f, and Example 19i the expected compound, mp 179°–181° C., was obtained.

EXAMPLE 19

N-(4-trifluoromethoxyphenyl)-3-(4-propoxyphenyl)-4-(N-methyl-N-(methoxycarbonyl)amino)-2,3,4,5-tetrahydro-1H-pyrazole-1-carboxamide a. 4-difluoromethoxyacetophenone

To 200 g (1470 mmole) of 4-hydroxyacetophenone dissolved in 1000 ml of dimethylformamide and cooled to 10° C. was added gaseous chlorodifluoromethane until the mixture was saturated. While vigorously mechanically stirring the mixture, 330 g (2600 mmole) of 45% aqueous potassium hydroxide was added while cofeeding chlorodifluoromethane to maintain an excess. The internal temperature was maintained at 10° C. during the addition. After standing overnight, the reaction mixture was carefully poured onto 5000 ml of water, gas was released! Extraction with a mixture of diethyl ether and hexanes, drying over anhydrous magnesium sulfate, and vacuum distillation yielded 173 g of 4-difluoromethoxyacetophenone, an oil, bp 65°–70° C. at 0.2 torr.

b. 2-bromo-4'-difluoromethoxyacetophenone

To 173 g (930 mmole) of 4-difluoromethoxyacetophenone dissolved in 150 ml of methylene chloride was added a few drops of bromine. The mixture was heated until the bromine color dissipated and then 25 ml of dioxane was added followed by 45 g (872 mmole) of bromine over the course of 30 minutes. Hydrogen bromide evolved. After the addition was complete the solvents are removed in vacuo and the product was taken up in diethyl ether and washed with water and brine. After drying over anhydrous magnesium sulfate the mixture was concentrated in vacuo and crystalized from 200 ml of 1:1 diethyl ether/hexanes yielding 164 g of the expected compound, a white solid, mp 64°–66° C.

c. 2-dimethylamino-4'-difluoromethoxyacetophenone

To 7.5 g (165 mmole) of anhydrous dimethylamine in 50 ml of methylene chloride and cooled to −30° C. was added a solution of 20 g (664 mmole) of 2-bromo-4'-difluoromethoxyacetophenone in 50 ml of methylene chloride. After the addition was complete the reaction was allowed to warm to 20° C. Concentration in vacuo, partitioning between diethyl ether and 1M aqueous sodium hydroxide, washing with brine, drying over anhydrous magnesium sulfate, and reconcentration in vacuo yielded 16.8 g of 2-dimethylamino-4'-difluoromethoxyacetophenone, an oil.

d. 2-(N-methyl-N-(methoxycarbonyl)amino)-4'-difluoromethoxyacetophenone

Method i

To 16.8 g (73 mmole) of 2-dimethylamino-4'-difluoromethoxyacetophenone in 100 ml of methylene chloride cooled to 0° C. was added 7.6 g (81 mmole) of methyl chloroformate. After the addition was complete the reaction mixture was allowed to warm to 20° C. and stirred overnight. Concentration in vacuo, partitioning between diethyl ether and 1M aqueous hydrochloric acid, washing with brine, drying over anhydrous magnesium sulfate, and reconcentration in vacuo gave a crude oil. Chromatography of this oil on silica gel using diethyl ether in hexanes gave 12 g of 2-(N-methyl-N-(methoxycarbonyl)amino)-4'-difluoromethoxyacetophenone an oil, bp 150°–190° C. at 0.7 torr.

Method ii

To 47 g (1510 mmole) of monomethylamine dissolved in 300 ml of methylene chloride and cooled to −20° C. was added a solution of 136 g (512 mmole) of 2-bromo-4'-difluoromethoxyacetophenone in 200 ml of methylene chloride. The internal temperature rose to 15° C. This mixture was allowed to stir for 15 minutes and then a solution of 40 g (500 mmole) of 50% aqueous sodium hydroxide in 100 ml of water was added. The resulting mixture was rapidly washed with two 500 ml portions of water. The resulting organic layer was cooled to 5° C. and 52 g (550 mmole) of methyl chloroformate and a mixture of 40 g (500 mmole) of 50% aqueous sodium hydroxide in 150 ml of water were simultaneously added with rapid stirring. The internal temperature was maintained between 0° C. and 10° C. After 10 minutes the organic layer was separated and washed with water and dilute aqueous hydrochloric acid. After drying over anhydrous magnesium sulfate, the methylene chloride was removed in vacuo and the diethyl ether soluble portion was filtered through silica gel. Concentration in vacuo yielded 90 g of the expected compound as a tan solid, mp 50°–52° C.

e. 2-(N-methyl-N-(methoxycarbonyl)amino)-1-(4-difluoromethoxyphenyl)-prop-2-enone To 9.1 g (33 mmole) of 2-(N-methyl-N-(methoxycarbonyl)amino)-4'-difluoromethoxyacetophenone in 100 ml of 1-propanol was added 5.3 g (66 mmole) of 37% formalin, 0.6 g of piperidine and 0.4 g of acetic acid. The mixture was refluxed for four hours, concentrated in vacuo, partitioned between diethyl ether and water, washed with brine, dried over anhydrous magnesium sulfate, and reconcentrated in vacuo, to yield 5.1 g of the expected compound, an oil.

f. N-(4-trifluoromethoxyphenyl)-3-(4-difluoromethoxyphenyl)-4-(N-methyl-N-(methoxycarbonyl)amino)-4,5-dihydro-1H-pyrazole-1-carboxamide To 3.1 g (10 mmole) of 2-(N-methyl-N-(methoxycarbonyl)amino)-1-(4-difluoromethoxyphenyl)prop-2-enone in 30 ml of methanol was added 0.2 g of acetic acid and 0.6 g (12 mmole) of hydrazine monohydrate. The mixture was refluxed for ten minutes, concentrated in vacuo, partitioned between diethyl ether and water, washed with brine, dried over anhydrous magnesium sulfate, and filtered. This yielded a diethyl ether solution of 3-(4-difluoromethoxyphenyl)-4-(N-methyl-N-(methoxycarbonyl)amino)-4,5-dihydro-1H-pyrazole which was not isolated. To this solution was added 2.0 g (10 mmole) of 4-trifluoromethoxyphenyl isocyanate. After refluxing for 1 hour the mixture was concentrated in vacuo and chromatographed over silica gel using diethyl ether and hexanes to yield 2.1 g of the expected compound, a white solid, mp 125°–126° C.

g. N-(4-trifluoromethoxyphenyl)-3-(4-hydroxyphenyl)-4-(N-methyl-N-(methoxycarbonyl)amino)-4,5-dihydro-1H-pyrazole-1-carboxamide To 25.5 g (50.8 mmole) of N-(4-trifluoromethoxyphenyl)-3-(4-difluoromethoxyphenyl)-4-(N-methyl-N-(methoxycarbonyl)amino)-4,5-dihydro-1H-pyrazole-1-carboxamide dissolved in 25 g of tetrahydrofuran and 25 g of t-butanol was added 10 g of potassium t-butoxide. The mixture was refluxed for 1 hour and an additional 3.5 g of potassium t-butoxide was added. After refluxing an additional hour the mixture was acidified with acetic acid, concentrated in vacuo, and partitioned between methylene chloride and water. The organic layer was dried over anhydrous magnesium sulfate, filtered, concentrated in vacuo, and chromatographed over silica gel using hexane and diethyl ether to yield the expected compound, a white solid, mp 228°–233° C.

h. N-(4-trifluoromethoxyphenyl)-3-(4-propoxyphenyl)-4-(N-methyl-N-(methoxycarbonyl)amino-4,5-dihydro-1H-pyrazole-1-carboxamide To 1.0 g (2.2 mmole) of N-(4-trifluoromethoxyphenyl)-3-(4-hydroxyphenyl)-4-(N-methyl-N-(methoxycarbonyl)amino)-4,5-dihydro-1H-pyrazole-1-carboxamide dissolved in 7.5 ml of dimethylsulfoxide was added 0.35 g (2.8 mmole) of 45% aqueous potassium hydroxide and 1.02 g (6.0 mmole) of 1-iodopropane. The mixture was warmed to 50° C. for 30 minutes and diluted with diethyl ether and water. The organic layer was washed with brine, dried over anhydrous magnesium sulfate, filtered, concentrated in vacuo, and chromatographed over silica gel using hexane and diethyl ether to yield the expected compound, a white solid, mp 153°–155° C.

i. N-(4-trifluoromethoxyphenyl)-3-(4-propoxyphenyl)-4-(N-methyl-N-(methoxycarbonyl)amino)-2,3,4,5-tetrahydro-1H-pyrazole-1-carboxamide To 5.2 grams (g) (10.6 mmole) of N-(4-trifluoromethoxyphenyl)-3-(4-propoxyphenyl)-4-(N-methyl-N-(methoxycarbonyl)amino)-4,5-dihydro-1H-pyrazole-1-carboxamide in 50 ml of tetrahydrofuran (THF) that had been cooled under a nitrogen atmosphere to −75° C. was added 28 ml of 1.0M diisobutylaluminum hydride (DIBAL-H) in THF. The reaction mixture was warmed to 20° C. and stirred for 5 hours. An additional 6 ml of the 1.0M DIBAL-H solution was added. After stirring at 20° C. overnight, the mixture was cooled to 0° C. and carefully quenched with 10 ml of methanol, a solid forms. Into this mixture was poured a mixture of 20 g of water and 10 ml of 12M aqueous hydrochloric acid. After the solid dissolved, the mixture was concentrated in vacuo and partitioned between diethyl ether and water. The organic layer was washed with dilute aqueous sodium hydroxide and brine and then dried over anhydrous magnesium sulfate, filtered and concentrated in vacuo. The resulting oil was chromatographed on silica gel using diethyl ether and hexanes to give the expected compound, an oil. NMR (200 MHz, CDCl$_3$) 1.1 t 3H, 1.8 sextet 2H, 2.6 s 3H, 3.6 s 3H, 4.0 t 2H, 4.1–4.6 m 3H, 5.5 bd 1H, 6.9 d 2H, 7.1 m 5H, 7.5 d 2H, 8.5 s 1H. Peaks exibit satellites due to hindered rotation.

Alternatively, compound 19h was prepared as follows:

j. 4'-propoxyacetophenone

To 272 g (2000 mmole) of 4'-hydroxyacetophenone dissolved in 800 ml of ethanol was added 249 g (2000 mmole) of 45% aqueous potassium hydroxide. After stirring for 5 minutes, 270 g (2200 mmole) of 1-bromopropane was added and the mixture was refluxed for 6 hours. After cooling, the precipitated potassium bromide was filtered off and washed with diethyl ether. The combined organic layers were concentrated in vacuo and then redissolved in 500 ml of diethyl ether. The resulting solution was washed with 1M aqueous sodium hydroxide solution and brine, dried over anhydrous magnesium sulfate, and concentrated in vacuo yielding 270 g of the expected product, an oil, bp 110° C. at 1 torr.

k. 2-(N-methyl-N-(methoxycarbonyl)amino)-4'-propoxyacetophenone

By substantially following the procedure given in Example 19b, substituting 2-(N-methyl-N-(methoxycarbonyl)amino)-4'-propoxyacetophenone for 2-(N-methyl-N-(methoxycarbonyl)amino)-4'-difluoromethoxyacetophenone and using diethyl ether as solvent and continuing with Example 19dii the expected compound, an oil, bp 150°–160° C. at 0.2 torr, was obtained.

l. 2-(N-methyl-N-(methoxycarbonyl)amino)-4'-propoxyphenyl-prop-2-enone

To 15.5 g (59 mmole) of 2-(N-methyl-N-(methoxycarbonyl)amino)-4'-propoxyacetophenone and 7.5 g (92 mmole) of formalin was added 3.5 g (58 mmole) of acetic acid and 3.5 g (41 mmole) of piperidine. The resulting mixture was refluxed for 2 hours, cooled, and partitioned between diethyl ether and water. The organic layer was washed with water and brine and dried over anhydrous magnesium sulfate. Concentration in vacuo gave the expected compound, an oil.

m. N-(4-trifluoromethoxyphenyl)-3-(4-propoxyphenyl)-4-(N-methyl-N-(methoxycarbonyl)amino)-4,5-dihydro-1H-pyrazole-1-carboxamide By substantially following the procedure of Example 19f substituting 2-(N-methyl-N-(methoxycarbonyl)amino)-4'-propoxyphenyl-prop-2-enone for 2-(N-methyl-N-(methoxycarbonyl)amino)-4'-difluoromethoxyphenyl-prop-2-enone the expected compound, identical to that of Example 19h, was obtained.

EXAMPLE 22

1-oxo-2-(4-trifluoromethylphenyl)-5-(4-chlorophenyl)-6-phenyl-1,2,3,4,6,7-hexahydro-5H-pyrazolo[1,2-a][1,2,4]triazole To 1.0 g (2.2 mmole) of N-(4-trifluoromethylphenyl)-3-(4-chlorophenyl)-4-phenyl-2,3,4,5-tetrahydro-1H-pyrazole-1-carboxamide in 5 ml of formic acid was added 0.57 g of formalin. The mixture was heated at reflux for 30 minutes and then partitioned between dichloromethane and water. The organic layer was washed with water and brine and then dried over anhydrous magnesium sulfate. Filtration, concentration in vacuo, and chromatography on silica gel using diethyl ether and hexanes gave the expected compound, mp 184°-187° C.

Example 23 was prepared following essentially the same procedure and using acetaldehyde in place of formalin.

EXAMPLE 24

1,3-dioxo-2-(4-trifluoromethylphenyl)-5-(4-chlorophenyl)-6-phenyl-1,2,3,4,6,7-hexahydro-5H-pyrazolo[1,2-a][1,2,4]triazole To 2.0 g (4.4 mmole) of N-(4-trifluoromethylphenyl)-3-(4-chlorophenyl)-4-phenyl-2,3,4,5-tetrahydro-1H-pyrazole-1-carboxamide (Example 3) in 5 ml of methylene chloride was added 4.2 ml (8 mmole) of 1.9M phosgene in toluene. After stirring for 5 minutes 0.8 g (10 mmole) of pyridine was added. The mixture was stirred for 1 hour and then partitioned between diethyl ether and dilute aqueous hydrochloric acid. The organic layer was washed with water and brine and then dried over anhydrous magnesium sulfate. Filtration, concentration in vacuo, and chromatography on silica gel using diethyl ether and hexanes gave the title compound, mp 148°-150° C.

Examples 21, 25 and 27 were prepared following essentially the same procedure starting from Examples 1, 3 and 13 and using oxalyl chloride in place of phosgene for Examples 25 and 27.

EXAMPLE 26

1,4-dioxo-2-(4-trifluoromethylphenyl)-6-(4-chlorophenyl)-7-phenyl-1,2,3,4,7,8-hexahydro-6H-pyrazolo[1,2-a][1,2,4]triazine To a suspension of 0.17 g (4.25 mmole) of 60% sodium hydride in mineral oil (twice washed with hexanes) in 5 ml of dimethyl formamide (DMF) was added 2.0 g (3.8 mmole) of N-(4-trifluoromethylphenyl)-3-(4-chlorophenyl)-4-phenyl-2-(2-chloroacetyl)-2,3,4,5-tetrahydro-1H-pyrazole-1-carboxamide (Example 8) dissolved in 5 ml of DMF. Gas was evolved. After stirring for 1 hour at 20° C. the solvent removed in vacuo and the residue was partitioned between ethyl acetate and water. The organic layer was washed with brine, dried over anhydrous magnesium sulfate, filtered, and concentrated in vacuo. Trituration of the resulting solid with ethyl ether/hexanes gave 1.4 g of product, mp 214°-216° C.

Example 28 was prepared following essentially the same procedure and starting from Example 14.

On the basis of their strong initial pesticidal activity and excellent residual pesticidal activity, compounds according to the invention may be used in low dosages in controlling pests. The amount of dosage depends on a variety of factors, for example, the substance used, the kind of pest, the formulation used, the state of the crop infested with the pest and the prevailing weather conditions. In general, for the control of pests in agriculture and horticulture, a dosage corresponding to from about 0.1 grams to about 1000 grams of the active substance per hectare may be used and from about 5 grams to about 200 grams per hectare of the active substance is preferred. The exact amount of dosage for a given situation can be routinely determined and depends on a variety of factors, for example, the substance used, the kind of pest, the formulation used, the state of the crop infested with the insect and the prevailing weather conditions.

The term "pesticidal" as employed in the specification and claims of this application is to be construed as any means which adversely affects the existence or growth of the target pest. Such means can compromise a complete killing action, eradication, arresting in growth, inhibition, reducing in number of any combination thereof. The term "control" as employed in the specification and claims of this application is to be construed as meaning "pesticidal" and protecting plants from pest damage. By "pesticidally effective amount" is meant that dosage of active substance sufficient to exert the desired pest "control".

Representative pests which can be controlled by the compounds of the present invention include:
American Cockroach (*Periplaneta americana*)
Bean Leaf Beetle (*Cerotoma trifurcata*)
Bean Leaf Roller (*Urbanus proteus*)
Black Carpenter Ant (*Camponotus pennsylvanicus*)
Black Cutworm (*Agrotis ipsilon*)
Boll Weevil (*Anthonomus grandis grandis*)
Colorado Potato Beetle (*Leptinotarsa decemlineata*)
Fall Armyworm (*Spodoptera frugiperda*)
German Cockroach (*Blattella germanica*)
Green June Beetle (*Cotinis nitida*)
House Cricket (*Acheta domesticus*)
Housefly (*Musca domestica*)
Mexican Bean Beetle (*Epilachna varivestis*)
Potato Leaf Hopper (*Empoasca fabae*)
Red Harvester Ant (*Pogonomyrmex barbatus*)
Red Imported Fire Ant (*Solenopsis invicta*)
Redlegged Grasshopper (*Melanopus femurrubrum*)
Southern Armyworm (*Spodoptera eridania*)
Southern Corn Rootworm (*Diabrotica undecimpunctata howardi*)
Tobacco Budworm (*Heliothis virescens*)

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredients effectiveness and which by itself has no significant detrimental effect on the soil, equipment, desirable plants, or agronomic environment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. Baits are preparations generally comprising a food or other substance attractive to insects, that includes at least one compound of the instant invention. The invert emulsions are mainly used for air application, where large areas are treated with a comparatively small amount of preparation and may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional pesticide dispersible liquid diluent carriers and/or dispersible solid carriers optionally with the use of carrier vehicle assistants such as conventional pesticide surface-active agents, including emulsifying agents and/or dispersing agents, for example, when water is used as diluent, organic solvents may be added as auxiliary solvents.

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001-99% by weight. For compositions suitable for storage or transportation, the amount of active ingredient is preferably between about 0.5-90% by weight, and more preferably between about 1-75% by weight of the mixture. Compositions suitable for direct application or field application generally cintain the active compound in an amount substantially between about 0.0001-95%, preferably between about 0.0005-90% by weight, and more preferably between about 0.001-75% by weight of the mixture.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

Compositions and formulations according to the present invention may also include known pesticidal compounds. This expands the spectrum of activity of the preparation and may give rise to synergism.

The following known insecticidal, fungicidal and acaricidal compounds are suitable for use in such a combined preparation. Insecticides such as:

acephate, acethion, acetoxon, aldicarb, aldoxycarb, aldrin, allethrin, allyxycarb, alpha-cypermethrin, amidithion, amitraz, amlure, anethol, azethion, azinphos-ethyl, azinphos-methyl, azocyclotin, bacillus thuringiensis, BCPE, bendiocarb, bensultap, benzoximate, benzyl acetate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chloropropylate, chlorphoxim, chlorpyrifos, chlorpyrifos methyl, chlorthiophos, clofentezine, CPCBS, CPMC, crotoxyphos, crufomate, cryolite, cufraneb, cyanofenphos, cyanophos, cyanthoate, cyfluthrin, cyhexatin, cypermethrin, cyphenothrin, cyromazine, DAEP, DDT, DDVP, deltamethrin, demeton, demeton-S-methyl, demeton-O-methyl, demeton-S, demeton-S-methyl sulfoxid, demephion-O, demephion-S, dialifor, diazinon, dicapthon, dichlofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, d-trans allethrin, endosulfan, endothion, endrin, entice, EPBP, EPN, esfenvalerate, ethiofencarb, ethion, ethoatemethyl, ethoprop, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, flufenoxuron, fluvalinate, fonofos, formetanate hydrochloride, formothion, fosmethilan, fosthietan, furathiocarb, furethrin, grandlure, heptachlor, HETP, hexythiazox, hydramethylnon, hydroprene, IPSP, isazophos, isobenzan, isofenphos, isoprocarb, isoprothiolane, isothioate, isoxathion, jodfenphos, kinoprene, lead arsenate, leptophos, lethane, lindane, lythidathion, malathion, mazidox, mecarbam, mecarphon, menazon, mephosfolan, methamidophos, methidathion, methiocarb, methomyl, methoprene, methoxychlor, methyl parathion, methyl phencapton, mevinphos, mexacarbate, MIPC, mirex, monocrotophos, MTMC, naled, nicotine, nonachlor, omethoate, ovex, oxamyl, oxydeprofs, oxydisulfoton, oxythioquinox, paraoxon, parathion, paris green, permethrin, perthane, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnell, rotenone, ryania, s-bioallethrin, salithion, schradan, sodium fluosilicate, sophamide, sulfotepp, sulprofos, tefluthrin, temephos, TEPP, terbufos, tetrachlorvinphos, tetradifon, tetramethrin, tetrasul, thallium sulfate, thiocarboxime, thiocyclamhydrogenoxalate, thiometon, tolclofos-methyl, toxaphene, triazophos, trichlorfon, trichloronate, triflumuron, trimethacarb, vamidothion, xylylcarb.

Fungicides which can be combined with the insecticides of this invention include:

(a) dithiocarbamate and derivatives such as ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as dinocap, binapacryl, and 2-sec-butyl-4,6-dinitrophenyl isopropyl carbonate;

(c) heterocyclic structures such as captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenasimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, alpha-[2-(4-chlorophenyl)ethyl]-alpha-phenyl-1H-1,2,4-triazole-1-propanenitrile, hexaconazole, cyproconazole, terbuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecyl-morpholine, dodemorph, and triforine;

(d) miscellaneous halogenated fungicides such as chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as griseofulvin, kasugamycin, polyoxin, validamycin, and streptomycin;

(f) copper-based fungicides such as copper hydroxide, cuprous oxide, basic cupric chloride, basic copper carbonate, copper terephthalate, copper naphthenate and Bordeaux mixture; and (g) miscellaneous fungicides such as dodine, phenylmercuric acetate, phenylmercuric monoethanol ammonium lactate, N-ethylmercuri-1,2,3,6-tetrahydro-3,6-endomethano-3,4,5,6,7,7-hexachlorophthalimide, p-dimethylaminobenzene sodium sulfonate, methylisothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

It has been found by biological evaluation that compounds according to the present invention have pesticidal activity and are capable of controlling larvae and adult forms of pests, especially insects from the orders Lepidoptera and Coleoptera. One skilled in the art will know how to determine the activity of a given compound against a given insect and the dosage required to obtain general or selective pesticidal effects. In addition, compounds of the present invention were found active against pyrethroid resistant pests such as the Colorado potato beetle and housefly.

In evaluating the pesticidal activity of the compounds of this invention, the following test procedures were employed.

Evaluations were made on the following insects:

| Common Name | Latin Name |
| --- | --- |
| Mexican Bean Beetle (MBB) | Epilachna varivestis |
| Southern Armyworm (SAW) | Spodoptera eridania |

A test solution containing 600 parts per million (ppm) was made by dissolving the test compound in a solvent (acetone:methanol, 1:1), adding a surfactant and then water to give an acetone:methanol:water system of 5:5:90. A 1:1 mixture of an alkylarylpolyetheralcohol (sold under the trademark Triton ® X-155) and a modified phthalic glycerol alkyl resin (sold under the trademark Triton ® B-1956) was utilized at the equivalent of 1 ounce per 100 gal. of test solution as a surfactant.

For the bean beetle and armyworm tests, individual bean (Phaseolus limensis var Woods' Prolific) leaves are placed on moistened pieces of filter paper in Petri dishes. The leaves are then sprayed with test solution using a rotating turntable and allowed to dry. The dishes are infested with 10 third instar larvae of Southern armyworm or Mexican bean beetle. The dishes are then covered.

The percent mortality for the bean beetle and armyworm evaluations are determined 96 hours after treatment. Evaluations are based on a scale of 0–100 percent in which 0 equals no activity and 100 equals total kill.

The rotating turntable consists of a fixed continuously operated spray nozzle under which targets are rotated at a fixed speed and distance. If the target is a Petri dish (such as for the armyworm), the distance from the nozzle is 15 inches. If the target is a Mason jar, the distance between the screened lid and the nozzle is 6 inches (10 inches from the base of the jar to the nozzle). The nozzle is located 8 inches from the rotating shaft. The targets on individual platforms revolve around the shaft at 1 revolution per 20 seconds but only a brief portion of this time occurs in the spray path. Targets pass only once under the nozzle and then are removed to drying hoods.

The nozzle used is a ¼ JCO Spraying Systems (Wheaton, Ill.) air atomizing nozzle equipped with a No. 2850 fluid cap and No. 70 air cap. At the 10 psig air pressure used with liquid siphon feed 0.5 GPH (gallons per hour) are delivered in a round spray pattern with a 21° spray angle. Targets are misted with spray droplets to the point that the droplets coalesce to form a uniform thin film insufficient to drown test organisms.

All treatments are maintained at 75°–80° F. under continuous fluorescent light in a well-ventilated room. The results of the initial pesticidal evaluations are given in Table III.

TABLE III

| Biological Evaluations Percent kill at 600 ppm | | |
| --- | --- | --- |
| Compound | Insect Species | |
| No. | SAW | MBB |
| 1. | 100 | 100 |
| 2. | 100 | 100 |
| 3. | 100 | 100 |
| 4. | 100 | 100 |
| 5. | 100 | 100 |
| 6. | 100 | 40 |
| 7. | 100 | 100 |

TABLE III-continued

Biological Evaluations
Percent kill at 600 ppm

| Compound No. | Insect Species | |
|---|---|---|
| | SAW | MBB |
| 8. | 100 | 100 |
| 9. | 100 | 100 |
| 10. | 100 | 100 |
| 11. | 100 | 100 |
| 12. | 100 | 100 |
| 13. | 100 | 100 |
| 14. | 100 | 100 |
| 15. | 100 | 100 |
| 16. | 100 | 100 |
| 17. | NT* | NT |
| 18. | NT | NT |
| 19. | NT | NT |
| 20. | 100 | 100 |
| 21. | 100 | 100 |
| 22. | 100 | 100 |
| 23. | 100 | 100 |
| 24. | 100 | 100 |
| 25. | 100 | 100 |
| 26. | 100 | 100 |
| 27. | 100 | 100 |
| 28. | 100 | 60 |

*NT means Not Tested

It is to be understood that changes and variations may be made without departing from the spirit and scope of the invention as defined by the appended claims.

What is claimed is:

1. A compound having the formula

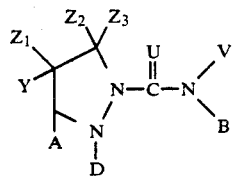

wherein

A and B are phenyl or phenyl substituted by one to three substituents independently selected from $(C_1-C_6)$alkyl, halo$(C_1-C_6)$alkyl, halo, $(C_1-C_6)$alkoxy, halo$(C_1-C_6)$alkoxy, $(C_3-C_6)$alkenyloxy, $(C_3-C_6)$alkynyloxy, $(C_1-C_6)$alkoxy$(C_1-C_6)$alkoxy, phenyl$(C_1-C_6)$alkoxy, phenyloxy, mono$(C_1-C_6)$alkylaminocarbonyloxy, di$(C_1-C_6)$alkylaminocarbonyloxy, $(C_1-C_6)$alkanoyloxy, $(C_1-C_6)$alkoxycarbonyloxy, $(C_1-C_6)$alkylsulfonyloxy, $(C_1-C_6)$alkylthio, halo$(C_1-C_6)$alkylthio, $(C_1-C_6)$alkoxy$(C_1-C_6)$alkyl, $(C_1-C_6)$alkanoyl, $(C_1-C_6)$alkoxycarbonyl, nitro, $(C_1-C_6)$alkylsulfonyl, halo$(C_1-C_6)$alkylsulfonyl, phenyl, hydroxy, cyano, isocyano, amino, mono$(C_1-C_6)$alkylamino, di$(C_1-C_6)$alkylamino, formylamino, $(C_1-C_6)$alkanoylamino, halo$(C_1-C_6)$alkanoylamino, $(C_1-C_6)$alkoxycarbonylamino, phenylcarbonylamino, mono$(C_1-C_6)$alkylaminocarbonylamino, and di$(C_1-C_6)$alkylaminocarbonylamino;

U is oxygen or sulfur;

V is hydrogen, $(C_1-C_6)$alkyl, $(C_1-C_6)$alkoxy$(C_1-C_6)$alkyl, formyl, $(C_1-C_6)$alkylcarbonyl, $(C_1-C_6)$alkylaminocarbonyl, $(C_1-C_6)$alkoxycarbonyl, $(C_3-C_6)$alkenyloxycarbonyl, phenyloxycarbonyl, $(C_1-C_6)$alkoxycarbonylcarbonyl, cyano$(C_1-C_6)$alkylthio, $(C_1-C_6)$alkylthio, phenylthio, $(C_1-C_6)$alkoxycarbonyl$(C_1-C_6)$alkylthio or $(C_1-C_6)$alkoxycarbonylthio;

D is hydrogen, phenylcarbonyl, halophenylcarbonyl, phenylsulfonyl, halophenylsulfonyl, $(C_1-C_6)$alkylsulfonyl, $(C_1-C_6)$alkanoyl, halo$(C_1-C_6)$alkanoyl, $(C_1-C_6)$alkoxycarbonyl or $(C_1-C_6)$alkyl;

Y is phenyl, halophenyl, $(C_1-C_6)$alkyl, halo$(C_1-C_6)$alkyl, hydroxy$(C_1-C_6)$alkyl, $(C_1-C_6)$alkoxy$(C_1-C_6)$alkyl, $(C_1-C_6)$alkoxy$(C_1-C_6)$alkoxy$(C_1-C_6)$alkyl, $(C_1-C_6)$alkylcarbonyloxy$(C_1-C_6)$alkyl, $((C_1-C_6)$alkylthio$)(C_1-C_6)$alkyl, $(C_1-C_6)$alkylsulfinyl$(C_1-C_6)$alkyl, cyano$(C_1-C_6)$alkyl, carboxy$(C_1-C_6)$alkyl, $(C_1-C_6)$alkoxycarbonyl$(C_1-C_6)$alkyl, $(C_2-C_6)$alkenyl, halo$(C_2-C_6)$alkenyl, formyl, $(C_1-C_6)$alkylcarbonyl, halo$(C_1-C_6)$alkylcarbonyl, phenylcarbonyl, $(C_1-C_6)$alkoxycarbonylcarbonyl, halocarbonyl, aminocarbonyl, N-$(C_1-C_6)$alkylaminocarbonyl, N,N-di$(C_1-C_6)$alkylaminocarbonyl, hydroxy$(C_1-C_6)$alkylaminocarbonyl, thio$(C_1-C_6)$alkylaminocarbonyl, phenylaminocarbonyl, carboxy, $(C_1-C_6)$alkoxycarbonyl, $(C_1-C_6)$alkoxy$(C_1-C_6)$alkoxycarbonyl, $(C_1-C_6)$alkoxy$(C_1-C_6)$alkoxy$(C_1-C_6)$alkoxycarbonyl, halo$(C_1-C_6)$alkoxycarbonyl, cyano$(C_1-C_6)$alkoxycarbonyl, $(C_1-C_6)$alkylthio$(C_1-C_6)$alkoxycarbonyl, $((C_1-C_6)$alkylthio$)$thiocarbonyl, isothiocyanato, isocyano, $-NR^1R^2$, $(C_1-C_6)$alkanoyloxy, $(C_1-C_6)$alkoxy, phenyloxy, $(C_1-C_6)$alkylthio, $(C_1-C_6)$alkylsulfonyl or phenylthio;

wherein $R^1$ and $R^2$ are independently hydrogen, cyano, $(C_1-C_6)$alkyl, halo$(C_1-C_6)$alkyl, cyano$(C_1-C_6)$alkyl, phenyl$(C_1-C_6)$alkyl, $(C_3-C_6)$alkenyl, halo$(C_3-C_6)$alkenyl, $(C_3-C_6)$alkynyl, phenyl, halophenyl, formyl, $(C_1-C_6)$alkylcarbonyl, halo$(C_1-C_6)$alkylcarbonyl, $(C_2-C_6)$alkenylcarbonyl, halo$(C_2-C_6)$alkenylcarbonyl, $(C_1-C_6)$alkoxy$(C_1-C_6)$alkylcarbonyl, phenylcarbonyl, phenyl$(C_2-C_6)$alkenylcarbonyl, carboxy, $(C_1-C_6)$alkoxycarbonyl, halo$(C_1-C_6)$alkoxycarbonyl, cyano$(C_1-C_6)$alkoxycarbonyl, $(C_2-C_6)$alkenyloxycarbonyl, $(C_3-C_6)$alkynyloxycarbonyl, $(C_1-C_6)$alkanoyl$(C_1-C_6)$alkoxycarbonyl, $(C_1-C_6)$alkoxycarbonyl$(C_1-C_6)$alkoxycarbonyl, carboxy$(C_1-C_6)$alkoxycarbonyl, phenyloxycarbonyl, phenyl$(C_1-C_6)$alkoxycarbonyl, $((C_1-C_6)$alkylthio$)$carbonyl, N-$(C_1-C_6)$alkylaminocarbonyl, N,N-di$(C_1-C_6)$alkylaminocarbonyl, N-phenyl-N-$(C_1-C_6)$alkylaminocarbonyl, N-(phenylcarbonyl)aminocarbonyl, di$(C_1-C_6)$alkylphosphoryl, $(C_1-C_6)$alkylsulfonyl, $(C_2-C_6)$alkenylsulfonyl, N,N-di$(C_1-C_6)$alkylaminosulfonyl, phenylsulfonyl, and $Z_1$ is hydrogen or $(C_1-C_6)$alkyl;
$Z_2$ is hydrogen or $(C_1-C_6)$alkyl;
$Z_3$ is hydrogen or $(C_1-C_6)$alkyl;

or an agronomically acceptable salt thereof.

2. The compound of claim 1 having the formula

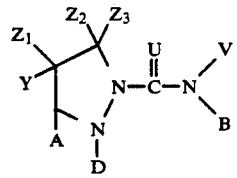

wherein

A and B are; phenyl or phenyl substituted by one to three substituents independently selected from $(C_1-C_6)$alkyl, halo$(C_1-C_6)$alkyl, halo, $(C_1-C_6)$alkoxy, halo$(C_1-C_6)$alkoxy, $(C_3-C_6)$alkenyloxy, ($C_3$-$C_6$)alkynyloxy, ($C_1$-$C_6$)alkoxy($C_1$-$C_6$)alkoxy, phenyl($C_1$-$C_6$)alkoxy, phenyloxy, mono($C_1$-$C_6$)alkylaminocarbonyloxy, di($C_1$-$C_6$)alkylaminocarbonyloxy, ($C_1$-$C_6$)alkanoyloxy, ($C_1$-$C_6$)alkoxycarbonyloxy, ($C_1$-$C_6$)alkylsulfonyloxy, ($C_1$-$C_6$)alkylthio, halo($C_1$-$C_6$)alkylthio, ($C_1$-$C_6$)alkoxy($C_1$-$C_6$)alkyl, ($C_1$-$C_6$)alkanoyl, ($C_1$-$C_6$)alkoxycarbonyl, nitro, ($C_1$-$C_6$)alkylsulfonyl, halo($C_1$-$C_6$)alkylsulfonyl, phenyl, hydroxy, cyano, isocyano, amino, mono($C_1$-$C_6$)alkylamino, di($C_1$-$C_6$)alkylamino, formylamino, ($C_1$-$C_6$)alkanoylamino, halo($C_1$-$C_6$)alkanoylamino, phenylcarbonylamino, mono($C_1$-$C_6$)alkylaminocarbonylamino, and di($C_1$-$C_6$)alkylaminocarbonylamino;

U is oxygen or sulfur;

V is hydrogen, ($C_1$-$C_6$)alkyl, ($C_1$-$C_6$)alkoxy($C_1$-$C_6$)alkyl, formyl, ($C_1$-$C_6$)alkylcarbonyl, ($C_1$-$C_6$)alkylaminocarbonyl, ($C_1$-$C_6$)alkoxycarbonyl, ($C_3$-$C_6$)alkenyloxycarbonyl, phenyloxycarbonyl, ($C_1$-$C_6$)alkoxycarbonylcarbonyl, cyano($C_1$-$C_6$)alkylthio, ($C_1$-$C_6$)alkylthio, phenylthio, ($C_1$-$C_6$)alkoxycarbonyl($C_1$-$C_6$)alkylthio or ($C_1$-$C_6$)alkoxycarbonylthio;

D is hydrogen, ($C_1$-$C_6$)alkoxycarbonyl, ($C_1$-$C_6$)alkylsulfonyl, ($C_1$-$C_6$)alkylcarbonyl or ($C_1$-$C_6$)alkyl;

Y is phenyl, halophenyl, ($C_1$-$C_6$)alkyl, halo($C_1$-$C_6$)alkyl, hydroxy($C_1$-$C_6$)alkyl, ($C_1$-$C_6$)alkoxy($C_1$-$C_6$)alkyl, ($C_1$-$C_6$)alkoxy($C_1$-$C_6$)alkoxy($C_1$-$C_6$)alkyl, ($C_1$-$C_6$)alkylcarbonyloxy($C_1$-$C_6$)alkyl, (($C_1$-$C_6$)($C_1$-$C_6$)alkyl, (($C_1$-$C_6$)alkylthio)($C_1$-$C_6$)alkyl, ($C_1$-$C_6$)alkylsulfinyl($C_1$-$C_6$)alkyl, cyano($C_1$-$C_6$)alkyl, carboxy($C_1$-$C_6$)alkyl, ($C_1$-$C_6$)alkoxycarbonyl($C_1$-$C_6$)alkyl, ($C_2$-$C_6$)alkenyl, halo($C_2$-$C_6$)alkenyl, formyl, ($C_1$-$C_6$)alkylcarbonyl, halo($C_1$-$C_6$)alkylcarbonyl, phenylcarbonyl, ($C_1$-$C_6$)alkoxycarbonylcarbonyl, halocarbonyl, aminocarbonyl, N-($C_1$-$C_6$)alkylaminocarbonyl, N,N-di($C_1$-$C_6$)alkylaminocarbonyl, hydroxy($C_1$-$C_6$)alkylaminocarbonyl, thio($C_1$-$C_6$)alkylaminocarbonyl, phenylaminocarbonyl, carboxy, ($C_1$-$C_6$)alkoxycarbonyl, ($C_1$-$C_6$)alkoxy($C_1$-$C_6$)alkoxycarbonyl, ($C_1$-$C_6$)alkoxy($C_1$-$C_6$)alkoxy($C_1$-$C_6$)alkoxycarbonyl, halo($C_1$-$C_6$)alkoxycarbonyl, cyano($C_1$-$C_6$)alkoxycarbonyl, ($C_1$-$C_6$)alkylthio($C_1$-$C_6$)alkoxycarbonyl, (($C_1$-$C_6$)alkylthio)thiocarbonyl, isothiocyanato, isocyano, —NR$^1$R$^2$, ($C_1$-$C_6$)alkanoyloxy, ($C_1$-$C_6$)alkoxy, phenyloxy, ($C_1$-$C_6$)alkylthio, ($C_1$-$C_6$)alkylsulfonyl or phenylthio;

wherein R$^1$ and R$^2$ are independently hydrogen, cyano, ($C_1$-$C_6$)alkyl, halo($C_1$-$C_6$)alkyl, cyano($C_1$-$C_6$)alkyl, phenyl($C_1$-$C_6$)alkyl, ($C_3$-$C_6$)alkenyl, halo($C_3$-$C_6$)alkenyl, ($C_3$-$C_6$)alkynyl, phenyl, halophenyl, formyl, ($C_1$-$C_6$)alkylcarbonyl, halo($C_1$-$C_6$)alkylcarbonyl, ($C_2$-$C_6$)alkenylcarbonyl, halo($C_2$-$C_6$)alkenylcarbonyl, ($C_1$-$C_6$)alkoxy($C_1$-$C_6$)alkylcarbonyl, phenylcarbonyl, phenyl($C_2$-$C_6$)alkenylcarbonyl, carboxy, ($C_1$-$C_6$)alkoxycarbonyl, halo($C_1$-$C_6$)alkoxycarbonyl, cyano($C_1$-$C_6$)alkoxycarbonyl, ($C_2$-$C_6$)alkenyloxycarbonyl, ($C_3$-$C_6$)alkynyloxycarbonyl, ($C_1$-$C_6$)alkanoyl($C_1$-$C_6$)alkoxycarbonyl, ($C_1$-$C_6$)alkoxycarbonyl($C_1$-$C_6$)alkoxycarbonyl, carboxy($C_1$-$C_6$)alkoxycarbonyl, phenyloxycarbonyl, phenyl($C_1$-$C_6$)alkoxycarbonyl, (($C_1$-$C_6$)alkylthio)carbonyl, N-($C_1$-$C_6$)alkylaminocarbonyl, N,N-di($C_1$-$C_6$)alkylaminocarbonyl, N-phenyl-N-($C_1$-$C_6$)alkylaminocarbonyl, N-(phenylcarbonyl)aminocarbonyl, di($C_1$-$C_6$)alkylphosphoryl, ($C_1$-$C_6$)alkylsulfonyl, ($C_2$-$C_6$)alkenylsulfonyl, N,N-di($C_1$-$C_6$)alkylaminosulfonyl, phenylsulfonyl, and $Z_1$ is hydrogen or ($C_1$-$C_6$)alkyl;
$Z_2$ is hydrogen or ($C_1$-$C_6$)alkyl;
$Z_3$ is hydrogen or ($C_1$-$C_6$)alkyl;

or an agronomically acceptable salt thereof.

3. The compound of claim 2 having the formula

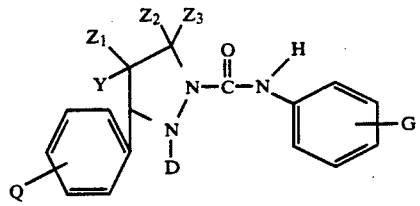

wherein

Q is hydrogen, halo, hydroxy, halo($C_1$-$C_6$)alkyloxy or ($C_1$-$C_6$)alkoxy;

G is halo, halo($C_1$-$C_6$)alkyl, ($C_1$-$C_6$)alkoxycarbonyl or halo($C_1$-$C_6$)alkoxy;

D is hydrogen, phenylcarbonyl, halophenylcarbonyl, phenylsulfonyl, halophenysulfonyl, ($C_1$-$C_6$)alkylsulfonyl, ($C_1$-$C_6$)alkanoyl, halo($C_1$-$C_6$)alkanoyl, ($C_1$-$C_6$)alkoxycarbonyl or ($C_1$-$C_6$)alkyl;

Y is hydrogen, ($C_1$-$C_6$)alkylaminocarbonyl, phenyl, halophenyl, ($C_1$-$C_6$)alkoxycarbonylamino or ($C_1$-$C_6$)alkoxycarbonyl(($C_1$-$C_6$)alkyl)amino;

$Z_1$ is hydrogen or ($C_1$-$C_6$)alkyl; and $Z_2$ and $Z_3$ are hydrogen.

4. The compound of claim 3 wherein

Q is hydrogen, 4-halo, 4-($C_1$-$C_6$)alkoxy or 4-halo($C_1$-$C_6$)alkoxy;

G is 4-halo, 4-halo($C_1$-$C_6$)alkyl or 4-halo($C_1$-$C_6$)alkoxy; and

Y is hydrogen, ($C_1$-$C_6$)alkylaminocarbonyl, phenyl, 4-halophenyl, ($C_1$-$C_6$)alkoxycarbonylamino or ($C_1$-$C_6$)alkoxycarbonyl(($C_1$-$C_6$)alkyl)amino.

5. The compound of claim 4 wherein

Q is 4-chloro, G is 4-trifluoromethyl, D is hydrogen, 4-chlorophenylcarbonyl, 4-chlorophenylsulfonyl, methoylsulfonyl, acetyl, chloroacetyl, methoxycarbonyl or methyl, $Z_1$ is hydrogen and Y is phenyl.

6. The compound of claim 4 wherein

Q is 4-chloro, G is 4-trifluoromethyl, D is hydrogen, $Z_1$ is methyl and Y is phenyl, hydrogen or methylaminocarbonyl.

7. The compound of claim 4 wherein

Q is 4-chloro, G is 4-trifluoromethyl, Y is 4-chlorophenyl, $Z_1$ is hydrogen and D is hydrogen, methoxycarbonylcarbonyl, chloroacetyl or 2-bromoethylcarbonyl.

8. The compound of claim 4 wherein

Q is 4-propoxy, G is 4-trifluoromethoxy, Y is methoxycarbonyl(methyl)amino, $Z_1$ is hydrogen and D is hydrogen.

9. The compound of claim 4 wherein

Q is 4-chloro, G is 4-trifluoromethoxy, $Z_1$ and D are hydrogen and Y is methoxycarbonylamino or methoxycarbonyl(methyl)amino.

10. An insecticidal composition which comprises an agronomically acceptable carrier and an insecticidally effective amount of the compound of claim 1.

11. An insecticidal composition which comprises an agronomically acceptable carrier and an insecticidally effective amount of the compound of claim 2.

12. An insecticidal composition which comprises an agronomically acceptable carrier and an insecticidally effective amount of the compound of claim 3.

13. An insecticidal composition which comprises an agronomically acceptable carrier and an insecticidally effective amount of the compound of claim 4.

14. An insecticidal composition which comprises an agronomically acceptable carrier and an insecticidally effective amount of the compound of claim 5.

15. An insecticidal composition which comprises an agronomically acceptable carrier and an insecticidally effective amount of the compound of claim 6.

16. An insecticidal composition which comprises an agronomically acceptable carrier and an insecticidally effective amount of the compound of claim 7.

17. An insecticidal composition which comprises an agronomically acceptable carrier and an insecticidally effective amount of the compound of claim 8.

18. An insecticidal composition which comprises an agronomically acceptable carrier and an insecticidally effective amount of the compound of claim 9.

19. The composition of claim 10 wherein the compound is present at from about 0.0001 to about 99 percent by weight of the composition.

20. The composition of claim 19, wherein the compound is present at from about 0.001 to about 90 percent by weight of the composition.

21. The composition of claim 20 wherein the compound is present at from about 0.01 to about 75 percent by weight of the composition.

22. The composition of claim 10 wherein the agronomically acceptable carrier is a solid.

23. The composition of claim 16 wherein the agronomically acceptable carrier is a liquid.

24. A method of controlling insects which comprises contacting the insects with an insecticidally effective amount of the compound of claim 1.

25. A method of controlling insects which comprises contacting the insects with an insecticidally effective amount of the compound of claim 2.

26. A method of controlling insects which comprises contacting the insects with an insecticidally effective amount of the compound of claim 3.

27. A method of controlling insects which comprises contacting the insects with an insecticidally effective amount of the compound of claim 4.

28. A method of controlling insects which comprises contacting the insects with an insecticidally effective amount of the compound of claim 5.

29. A method of controlling insects which comprises contacting the insects with an insecticidally effective amount of the compound of claim 6.

30. A method of controlling insects which comprises contacting the insects with an insecticidally effective amount of the compound of claim 7.

31. A method of controlling insects which comprises contacting the insects with an insecticidally effective amount of the compound of claim 8.

32. A method of controlling insects which comprises contacting the insects with an insecticidally effective amount of the compound of claim 9.

33. The method of claim 24 wherein the compound is applied at from about 0.10 g to about 1000 g per hectare.

34. the method of claim 33 wherein the compound is applied at from about 5 g to about 200 g per hectare.

* * * * *